US009820891B2

(12) United States Patent
Abir

(10) Patent No.: US 9,820,891 B2
(45) Date of Patent: Nov. 21, 2017

(54) SENSOR FOR URINE AND STOOL DETECTION

(71) Applicants: Digisense Ltd., Petach Tikva (IL); Expro3, LLC., Coral Gables, FL (US)

(72) Inventor: Eyall Abir, Petach Tikva (IL)

(73) Assignees: Digisense Ltd, Petach Tikva (IL); Expro3, LLC, Coral Gables, FL (US)

( * ) Notice: Subject to any disclaimer, the term of this patent is extended or adjusted under 35 U.S.C. 154(b) by 0 days.

(21) Appl. No.: 14/448,061

(22) Filed: Jul. 31, 2014

(65) Prior Publication Data

US 2015/0150732 A1 Jun. 4, 2015

Related U.S. Application Data

(60) Provisional application No. 61/860,277, filed on Jul. 31, 2013.

(51) Int. Cl.
*A61F 13/42* (2006.01)
*G01N 27/22* (2006.01)
*G01N 21/55* (2014.01)
*A61F 5/48* (2006.01)

(52) U.S. Cl.
CPC ............. *A61F 13/42* (2013.01); *A61F 5/48* (2013.01); *G01N 21/55* (2013.01); *G01N 27/228* (2013.01); *A61F 2013/424* (2013.01); *G01N 2201/062* (2013.01)

(58) Field of Classification Search
CPC ...... G01N 21/55; G01N 27/228; A61F 13/42; G08B 23/00
See application file for complete search history.

(56) References Cited

U.S. PATENT DOCUMENTS

| 5,903,222 A * | 5/1999 | Kawarizadeh ....... G01N 27/223 128/886 |
| 2005/0195085 A1* | 9/2005 | Cretu-Petra .......... A61B 5/6808 340/573.5 |
| 2010/0168694 A1* | 7/2010 | Gakhar ................... A61F 13/42 604/361 |
| 2010/0328075 A1* | 12/2010 | Rahamim ............ A61B 5/1135 340/573.1 |

* cited by examiner

*Primary Examiner* — Jermele M Hollington
*Assistant Examiner* — Zannatul Ferdous
(74) *Attorney, Agent, or Firm* — Greenberg Traurig, LLP

(57) ABSTRACT

A sensor for detecting urine and stool secretion mounted over two or more layers of garment, said sensor comprising: at least one light source configured to illuminate said garment; at least one photodetector configured to output an indication of the amount of light reflected from said garment; and an electronic circuit configured to detect said secretion by monitoring said output of said photodetector and identifying a temporal pattern being characteristic of said secretion event.

10 Claims, 50 Drawing Sheets

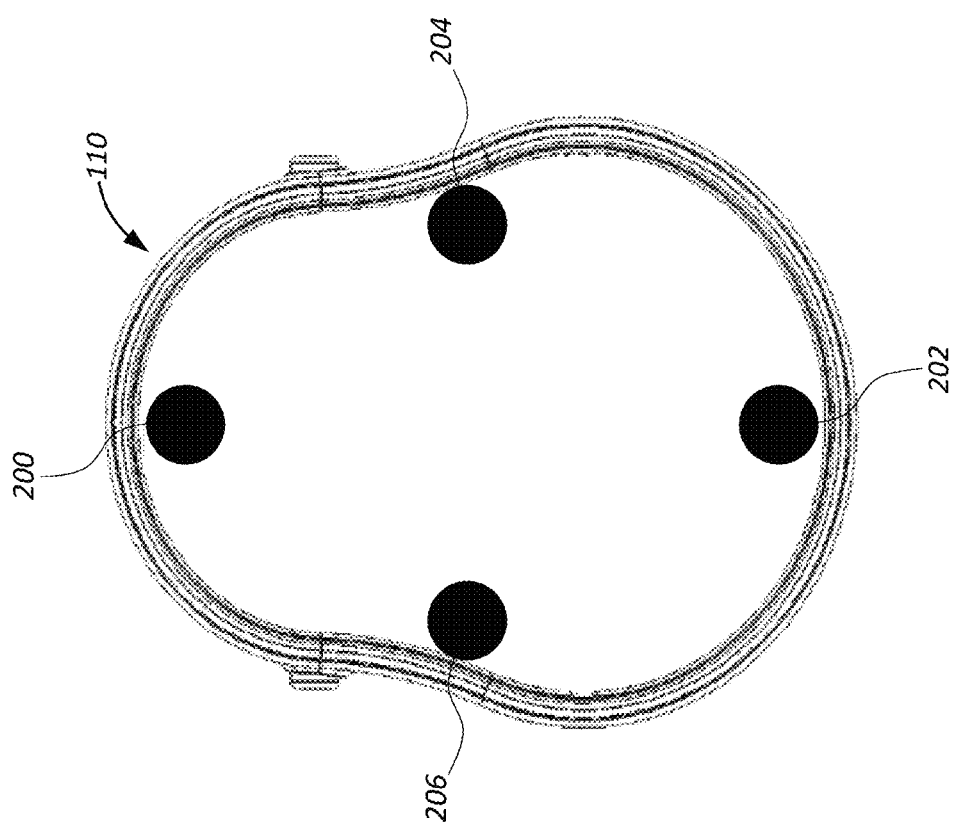

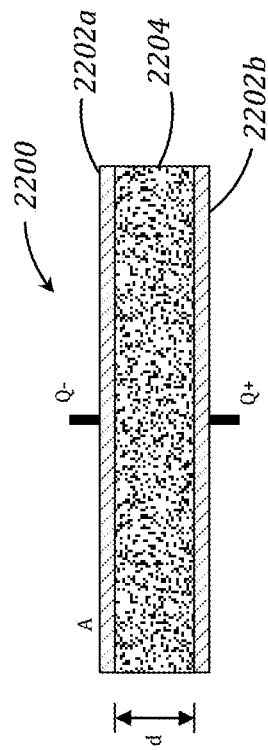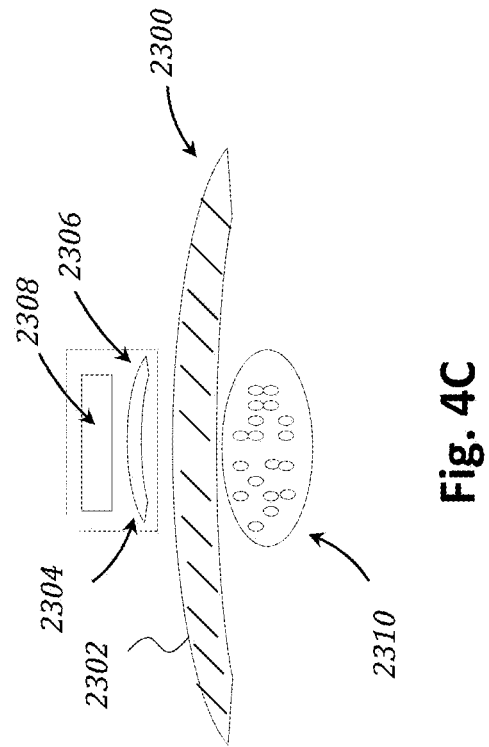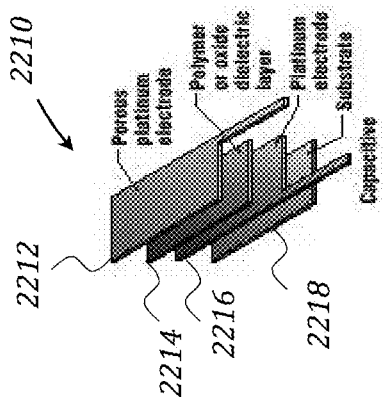

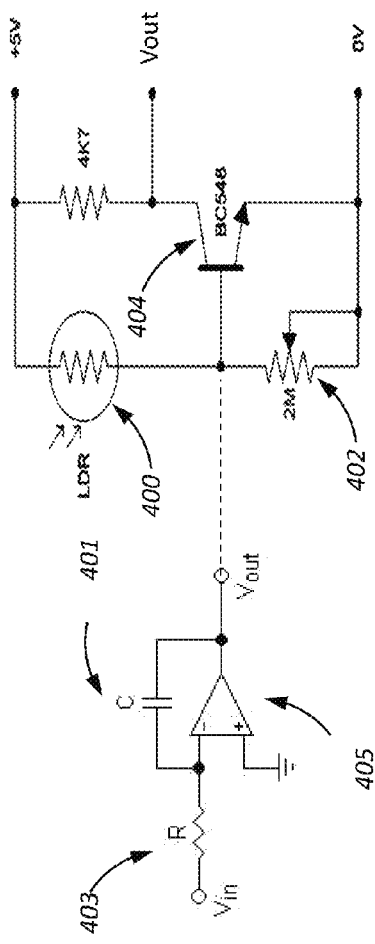
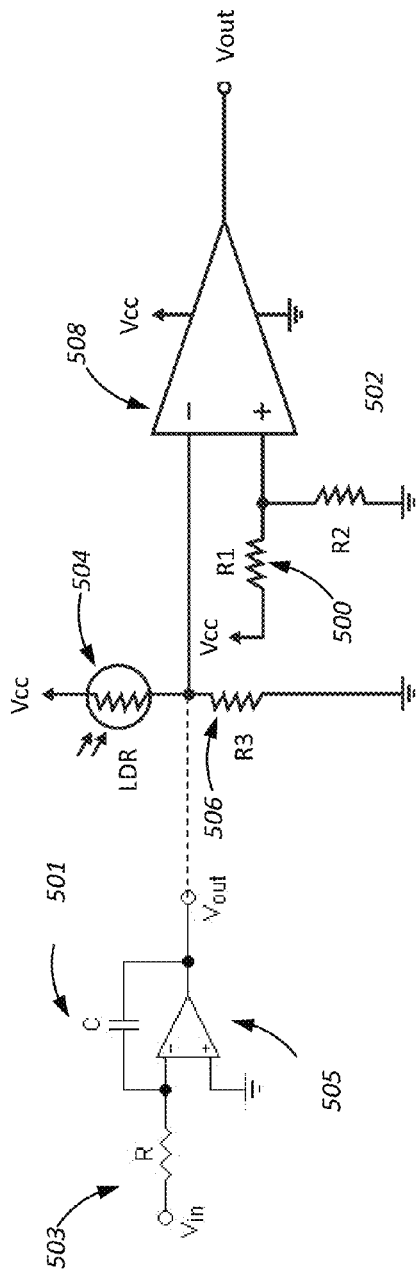
Fig. 6
Fig. 7

SENSOR FOR URINE AND STOOL DETECTION

FIELD OF THE INVENTION

The invention relates to sensors for urine and stool detection.

BACKGROUND

Various systems and devices for infant and adult incontinency monitoring have been previously proposed and implemented to monitor the condition of a diaper, bedding, adult incontinence brief and other similar articles. Today's parents also have an increased desire to instantly know when their infant's diaper is wet or soiled.

Common drawbacks of many existing detection systems are their size, complexity and reliability. There is still an unmet need for devices, systems and methods for monitoring urine and stool secretion of a subject, and optionally alerting a caregiver as to the secretion.

U.S. Pat. No. 4,796,014 to Chia discloses a urine-detecting device adapted to be associated with a baby's diaper, detects and signals the presence of urine after a sufficient time delay from the initiation of urination so as not to interfere with the baby's act of urination. The signal is audio and optionally with visual. The device is aiming at safety, compactness and convenience. It combines sensing means and fastening means with signaling means attached to it. A fastening means such as a safety pin with spaced apart electrical conductors on it is used to engage the device to a diaper. When urine bridges the space between the conductive a detection circuit is completed which activates the signal.

U.S. Patent Application Publication No. 2012/0310192 to Suzuki et al. discloses an excretion detection device that includes a power supply unit having an electrode and an electrode configured by using materials having different ionization tendencies; a solution retention unit configured to retain an electrolyte solution, a temperature sensor configured to detect the temperature information, and an active tag including a radio transmission unit configured to transmit the temperature information detected by the sensor to outside the excretion detection device. The electrode and the electrodes are installed at a position where the electrodes can be in contact with the bodily waste and the electrolyte solution, and can also be in contact with the electrolyte solution before the excretion of the bodily waste.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a sensor for detecting urine and stool secretion mounted over two or more layers of garment, said sensor comprising: at least one light source configured to illuminate said garment; at least one photodetector configured to output an indication of the amount of light reflected from said garment; and an electronic circuit configured to detect said secretion by monitoring said output of said photodetector and identifying a temporal pattern being characteristic of said secretion event.

There is further provided, in accordance with an embodiment, a sensor for detecting urine and stool secretion mounted over two or more layers of garment, said sensor comprising: at least one capacitive detector, said detector configured to output an indication of the magnitude of the capacitance of said capacitive detector; and an electronic circuit configured to detect said secretion by monitoring said output of said capacitive detector and identifying a temporal pattern being characteristic of said secretion event.

In some embodiments, the sensor further comprises a curved bottom shape.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 3 shows an illustration of a distribution of detectors on the backside of a sensor;

FIG. 4A shows a cross-sectional view of an exemplary capacitor;

FIG. 4B shows an exploded view of an exemplary capacitive detector;

FIG. 4C shows a cross-sectional view of a capacitive detector mounted on a diaper, while the diaper is soiled with a secretion;

FIG. 6 shows a schematic circuit of a capacitive or LDR detector connected to transistor converter/conditioner;

FIG. 7 shows a schematic circuit of a capacitive or LDR sensor connected to comparator converter/conditioner;

DETAILED DESCRIPTION

Disclosed herein are a device and a system for sensing and monitoring urine and stool secretion. One or multiple sensors may be attached to, worn on, embedded in or integrally formed with a wearable garment, such as a disposable infant diaper, pants, overall, baby strollers, baby cribs, baby swings, baby bouncers, adult incontinence product, etc. in order to sense urine and stool secretion of the wearer. Furthermore, in some embodiments, sensing of the urine and stool is performed through a plurality of garment layers, for example through a diaper and pants worn over the diaper. Advantageously, the present sensor(s) detect urine and stool secretion using optical and/or capacitive means.

The sensing of urine and stool secretion may be advantageous, in particular, for un-weaned infants as well as for certain individuals who suffer incontinence problems. For example, parents of an un-weaned infant may desire to be able to monitor such parameters and be alerted when a change occurs.

The sensor may output an alert, such as an audio, visual and/or tactile alert, when urine and stool secretion may be detected. In an embodiment, a photodetector (also "light sensor") such as CCD, CMOS, LDR (Light Dependent Resistor), photovoltaic cell, photodiodes (operative in photovoltaic mode or photoconductive mode), phototransistor, etc may be used for detecting urine and stool secretion, based on the principle of a varying output signal dependant on reflected light, which varies due to urine and stool absorption in the diaper. In another embodiment, a capacitive detector such as implemented in humidity sensors may be used for detecting urine and stool secretion, based on the principle of a varying output signal dependant on capacitance which varies due to urine and stool absorption in the diaper.

Figure 1:
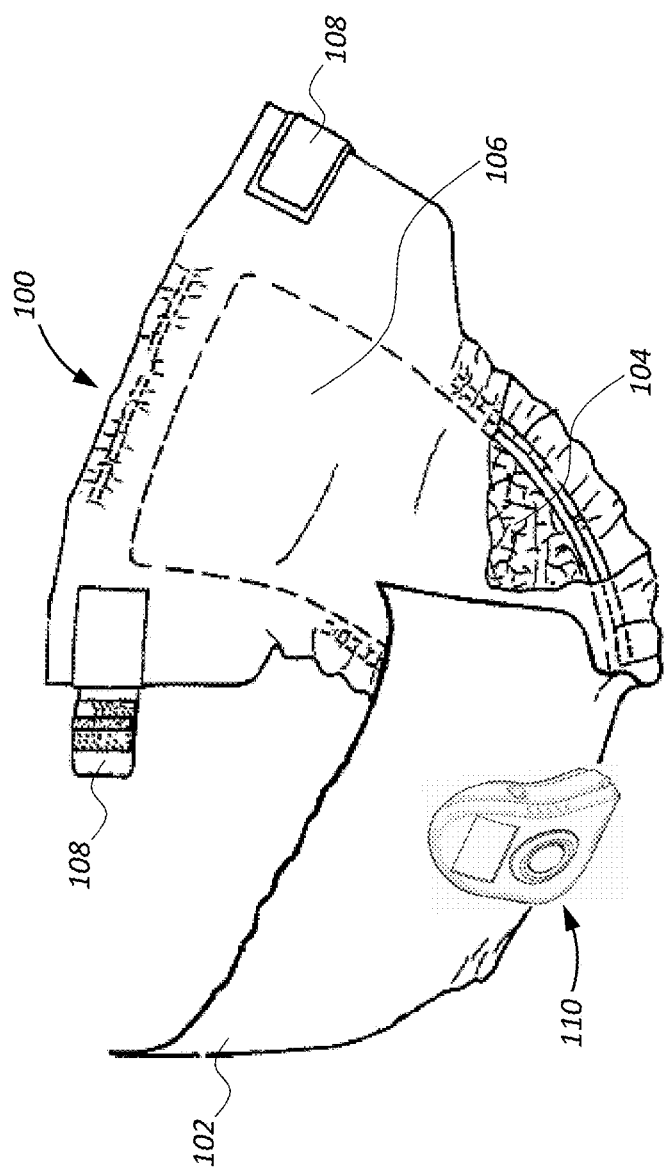
FIG. 1 shows an illustration of a diaper equipped with a sensor.
Figure 2A:
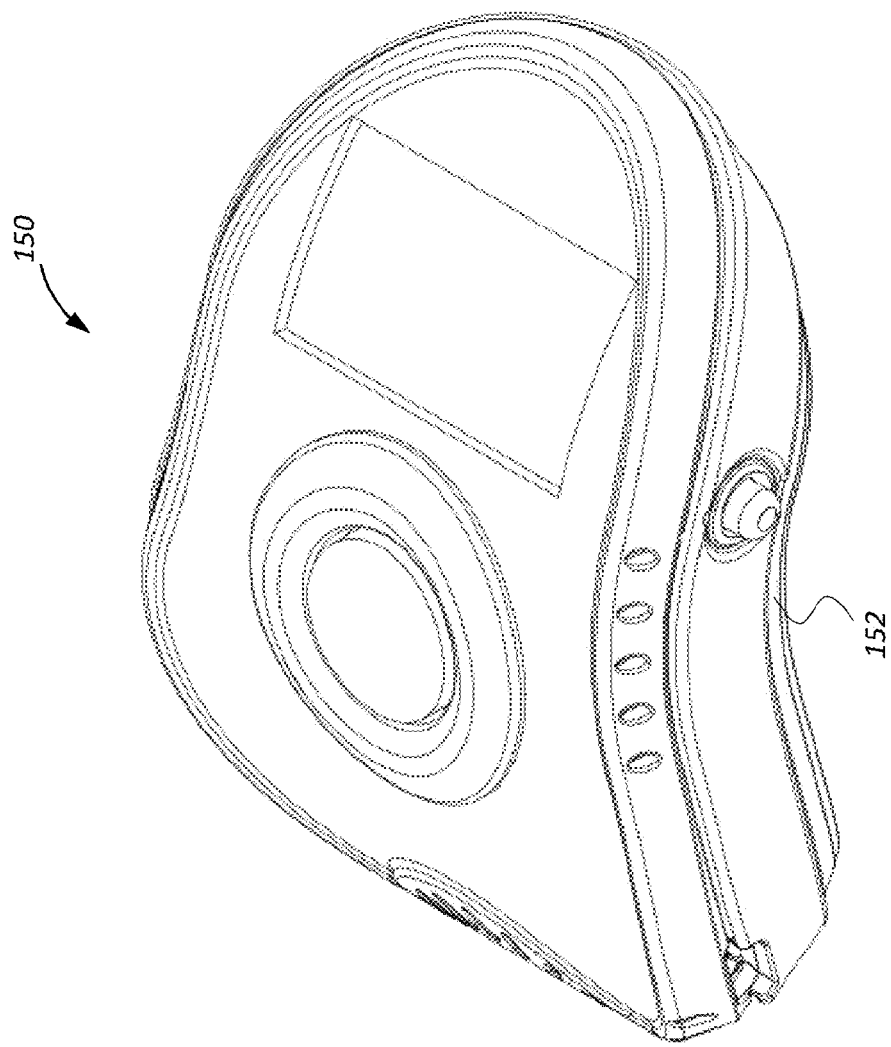
FIG. 2A shows an illustration of a close up perspective view of an exemplary sensor.
Figure 2B:
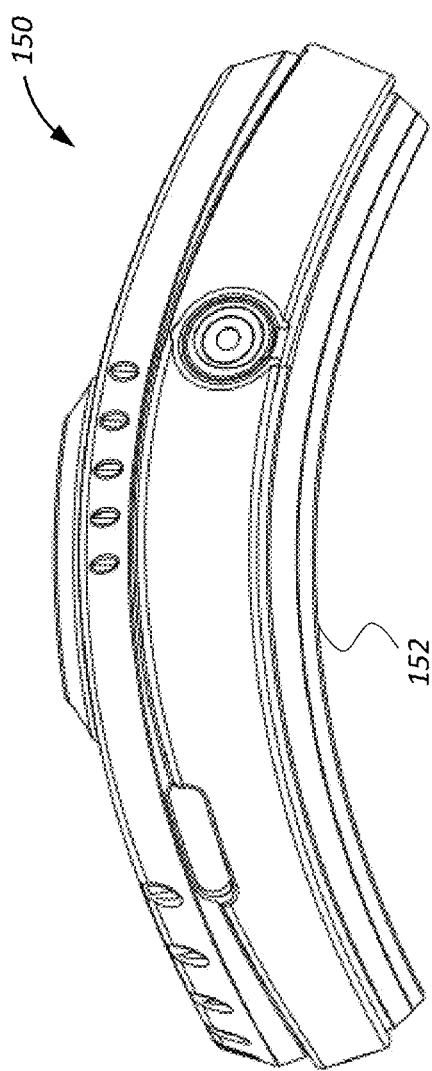
FIG. 2B shows an illustration of a close up perspective side view of the sensor of FIG. 2A.

The present disclosure may be better understood with reference to the accompanying figures. Reference is now made to FIG. 1, which shows an illustration of a diaper equipped with a urine and or stool sensor. The basic layers found in many modern diapers, such as diaper 100, are commonly: (a) an outer shell 102, commonly made of a breathable polyethylene film or a nonwoven and film composite, which prevents wetness and soil transfer to the outside environment; (b) an inner absorbent layer 104, usually containing a mixture of air-laid paper and superabsorbent polymers; and (c) a layer 106 nearest the skin, oftentimes made of a nonwoven material with a distribution layer directly beneath, which transfers wetness to the absorbent layer. A pair of fasteners 108 is commonly used to close the diaper around the wearer's abdomen. In an embodiment, diaper 100 may embed on outer shell 102 a sensor 110, which includes one or more detector, and an electronic circuit (not shown here). If optical detectors are used, then the sensor may further include one or more illuminators such as LEDs (Light Emitting Diode). Sensor 110 may be positioned on the front bottom of the diaper, which covers the infant's groin. Reference is now made to FIGS. 2A and 2B, which show perspective views of an exemplary sensor 150. A housing of sensor 150 have a curved bottom shape 152, for better fitting to the curved groin shape, and for implying the infant caregiver where to locate sensor 150 on a diaper (not shown). With reference back to FIG. 1, components of sensor 110 may be distributed in different layers and/or in different positions. The detectors may be positioned such that their sensing surface is directed towards the inside of diaper 100, and the LEDs (in case photodetectors are used) may be positioned such that their light emission is also directed towards the inside of diaper 100. Also, the detectors may be variously located upon sensor 110, enabling differential sensing upon diaper 100 and more enhanced calculation. Reference is now made to FIG. 3 which shows an illustration of a distribution of detectors on the backside of sensor 110. Sensor 110 may include a top detector 200, a bottom detector 202, a right detector 204, and a left detector 206 with respect to the infant's body. The distribution of the detectors is such to allow a proper coverage of the relevant area of the diaper. Thus, the position and distribution of the detectors is also dependent on the specific characteristics of the detectors. For example, bottom detector 202 is better positioned for stool detection.

In some embodiments, a capacitive sensor is used as a sensor for detecting urine secretion and/or stool secretion. Reference is now made to FIGS. 4A, 4B and 4C. FIG. 4A shows a cross-sectional view of an exemplary capacitor 2200. Capacitor 2200 includes two metal conductive plates 2202a and 2202b, which are separated by a dielectric material 2204. The capacitance C is given by:

$$C = \frac{\varepsilon_0 \varepsilon_r A}{d},$$

where:

A is the area of overlap between the two plates;
$\in_r$ is the relative static permittivity (also known as the dielectric constant) of the material between the plates (for a vacuum, $\in_r=1$);
$\in_0$ is the electric constant ($\in_0 \approx 8.854 \times 10^{-12}$ F m$^{-1}$); and
d is the distance between the plates.

FIG. 4B shows an exploded view of an exemplary capacitive detector 2210. Capacitive detectors are typically built on a substrate of glass, ceramic, or silicon (substrate 2218). A dielectric layer 2214 made from a thin polymer film or a metal oxide is placed between two metal electrodes 2212 and 2216. The surface electrode 2212 is porous.

Urine and stool may be considered as having the characteristics of an electrolyte solution. Hence, they may influence the electrical field in their surroundings. Reference is now made to FIG. 4C, which shows a cross-sectional view of a capacitive detector 2304 mounted on a diaper 2302, while the diaper is soiled with a secretion 2310. Capacitive detector 2304 includes a porous electrode 2306 and capacitive element 2308. Capacitive detector 2304 is coupled with the outer shell 2302 of diaper 2300. Porous electrode 2306 and secretion 2310 serve here as the 2202a and 2202b plates of capacitor 2200 of FIG. 4A accordingly. Outer shell with internal diaper absorption material 2302 serves here as dielectric layer 2204 of capacitor 2200 of FIG. 4A. Such configuration implements the physics of a capacitor and may be referred to as a "diaper capacitor". Thus, the "diaper capacitor" is connected in series with capacitive element 2308 of detector 2304.

In order to detect the capacitance in steady state and during change, detector 2304 is coupled with suitable electronics (not shown). The electronics are either embedded in the diaper during the manufacturing process, or externally coupled with the diaper, e.g. with the outer shell of the diaper.

Since secretion 2310 appears to be a part of the capacitor of the diaper, it may immediately influence the capacitance magnitude of capacitive detector 2304.

In some embodiments, a photodetector is used as a sensor for detecting urine secretion and/or stool secretion. As urine and/or stool are secreted into the diaper, the amount of light reaching a photodetector decreases, since a greater portion of the light may now be blocked by the secretions. Generally, the amount of light reaching the photodetector changes as a function of the amount of urine and/or stool disposed inside the diaper. An LDR sensor may be based on the principle of a decreasing resistance when light incidence increases.

Figure 5:
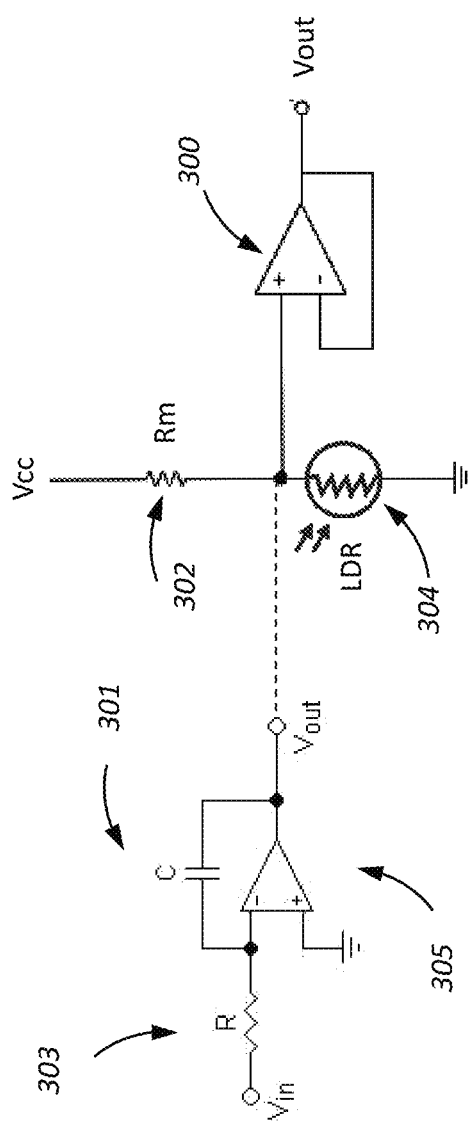
FIG. 5 shows a schematic circuit of a capacitive or LDR detector connected to operational amplifier converter/conditioner.

Reference is now made to FIG. 5 which shows a schematic circuit of LDR detector 304 or a capacitor 301 connected to operational amplifier converter/conditioner. The operational amplifier 300 may have high input impedance and unity gain, and if LDR 304 is used, the principle may be based on a voltage divider between a fixed resistor 302, referred also as $R_m$, and LDR 304, referred also as $R_{photo}$. The output voltage $V_{out}$ may be given by $$V_{out} = \frac{V_{cc}}{(1 + R_m/R_{photo})},$$

i.e. output voltage is rather linear to LDR resistance. Alternatively, an integrator circuit including capacitive sensor 301, resistor 303 and amplifier 305 may be used (instead of resistor 302 and LDR 304). The value of the output voltage (indicated Vout) depends on the value of capacitive sensor charge or discharge 301 as a function of time.

Reference is now made to FIG. 6 which shows a schematic circuit of LDR detector 400 or capacitive sensor 401 connected to transistor converter/conditioner. An LDR 400 and a 2MΩ resistor 402 may serve as a voltage divider. When light level is low (in our case, when pieces are interlocked), the resistance of LDR 400 may be high. This may prevent current from flowing to the base of the transistor 404. Consequently, the output voltage may be low, commonly close to 0 volts. However, when light illuminates the LDR without much interference (in our case, when pieces are not interlocked) the resistance may fall and current may flow into the base of transistor 404, increasing the output voltage to high level (about 5 volts). Alternatively, an integrator circuit including capacitive sensor 401, resistor 403 and amplifier 405 may be used (instead of resistor 402 and LDR 400).

Reference is now made to FIG. 7 which shows a schematic circuit of LDR detector 504 or capacitive sensor 501 connected to comparator converter/conditioner. Resistor 500, referred also as $R_1$, and Resistor 502, referred also as $R_2$, may serve as voltage divider with a known preset level. The LDR 504 and resistor 506, also referred as $R_3$, may also serve as voltage divider. When the voltage of the negative pole (−) of the operational amplifier 508 may be smaller than the positive pole input voltage (+), then $V_{out}$ may be set to high level. When the voltage of the negative pole (−) may be greater than the positive pole input voltage (+), then $V_{out}$ may be set to low level. Alternatively, an integrator circuit including capacitor 501, resistor 503 and amplifier 505 may be used (instead of resistor 506 and LDR 504).

Figure 8:
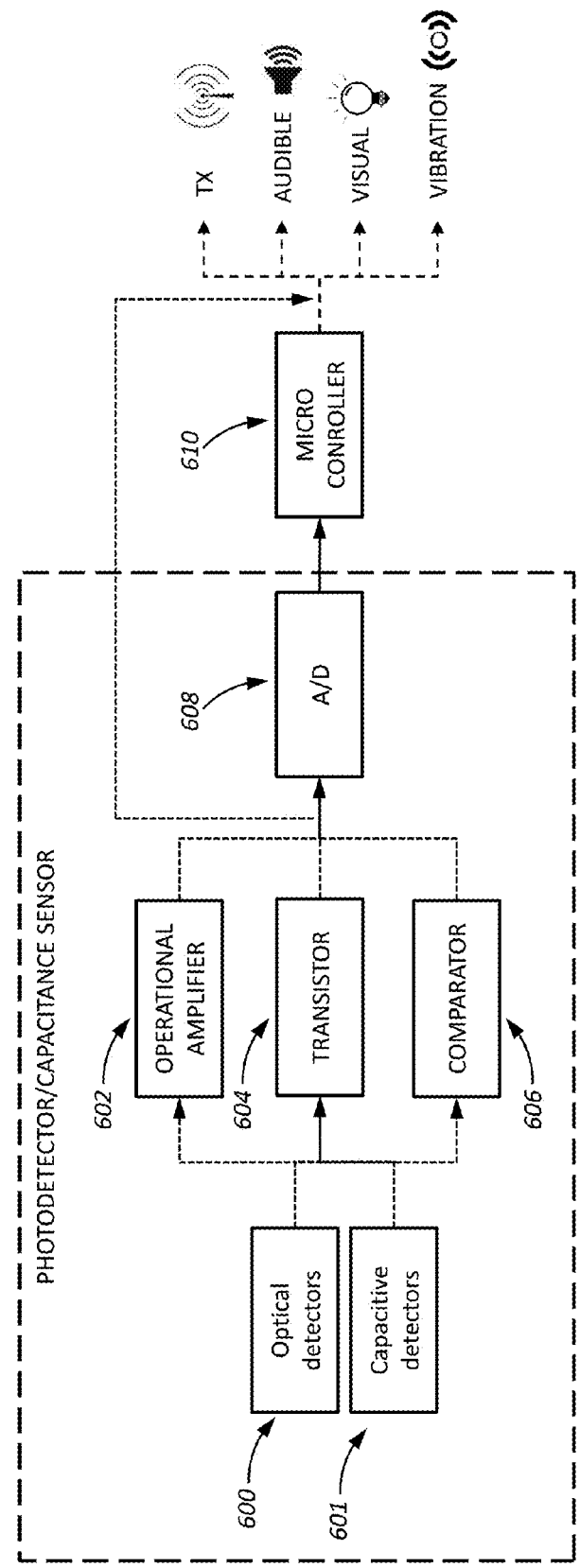
FIG. 8 shows a block diagram of an exemplary sensor.

Reference is now made to FIG. 8, which shows a block diagram of a sensor based on exemplary LDR-based photodetectors and/or capacitive detectors. As described before, a sensor may include optical detectors 600 or capacitive detectors 601 which may be coupled with one of multiple components: an operational amplifier 602, a transistor 604, or a comparator 606. The signal may be then transferred through an ADC (Analog to Digital) converter 608, and may be fed to a microcontroller 610 (e.g., P/N:PIC18F46J50 made by Microchip) for further processing. Alternatively, one of the multiple components may be directly coupled in simplicity with a notification element. Microcontroller 610 may collect the signals of two or more detectors 600 and 601 to compute existence of urine and/or stool secretion, and in case of detection, trigger an output. Microcontroller 610 may perform an exemplary algorithm for detecting urine and stool secretion.

For any implementation, the output may be in a form of a vibration alert, and/or visual alert, and/or vocal alert, and/or transmit alert indication to a distant receiver (not shown here).

The described photodetector and a capacitance detector in this paper are using analog output interface. There are many kinds of detector parameters as for example output signal topologies, like various analog and digital interfaces which can be use. Such as for example of digital interfaces are: I2C,SPI, 1-wire, etc.

The described photodetector and a capacitance detector in this paper are using analog output interface. There are many kinds of detector parameters as for example output signal topologies, like analog and digital interfaces which can be use.

According to some embodiments, the sensor disclosed herein may further interface and/or communicate with an external and/or remote device to convey a signal generated by the sensor(s) disclosed herein to the device (herein, a "receiver" or a "receiving device"). Conveying the signal from the sensor of the sensing device to the receiving device may be performed by various communication routes, such as radio frequency or acoustic communication. Acoustic communication makes use of sound and/or ultrasound, whereby a "transmitter" produces a sound that is detected by a "receiver". Sound is produced by the transmitter when a physical object vibrates rapidly, disturbs nearby air molecules (or other surrounding medium) and generates compression waves that travel in all directions away from the source. Sound can be made to vary in frequency (high pitch vs. low pitch), amplitude (loudness), and periodicity (the temporal pattern of frequency and amplitude). Since acoustic waves move rapidly through the medium, acoustic signals can be quickly started, stopped, or modified to send a time-sensitive message.

Figure 9:
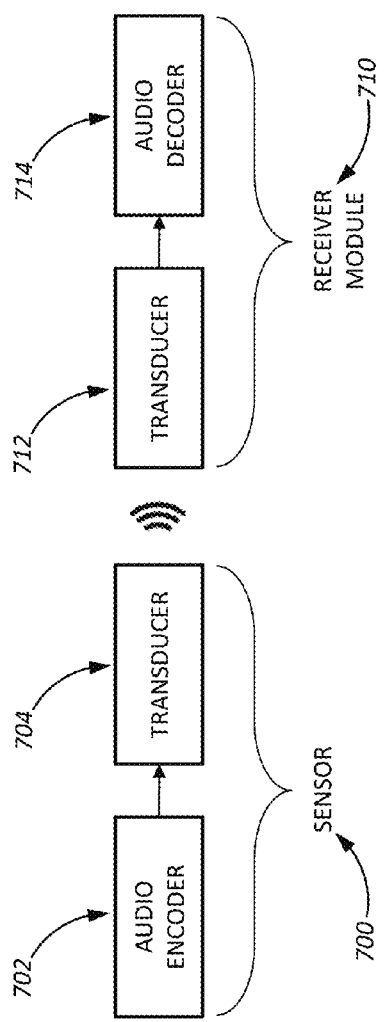
FIG. 9 shows a schematic illustration of an exemplary acoustic communication interface between a sensing device and a receiving device.

Reference is now made to FIG. 9, which shows a schematic illustration of an exemplary acoustic communication interface between a sensing device and a receiving device. Sensing device 700 includes an audio encoder 702, adapted to produce an acoustic signal based on the signal produced by the sensor. Audio encoder 702 may be incorporated in the microcontroller discussed earlier, or be coupled with it. The sensing device further includes a transducing element 704, adapted to convert an electrical signal from audio encoder 702 into an acoustic signal transmitted towards the remote receiver. In some exemplary embodiments, the transducing element 704 is a speaker. The acoustic signal produced by the sensing device may then be detected by transducer unit 712 of receiving device 710. In some exemplary embodiments, transducer 712 is a microphone. The acoustic signal may then be decoded by audio decoder 714 of the receiving device. Decoding the acoustic signal may be used to convert the acoustic signal to an electrical signal. The decoded signal may be processed and conveyed to a user. In some embodiments, the decoded signal may be converted to an alarm signal that may be a visual signal, a tactile signal, an audible signal, and the like, or any combination thereof.

According to some embodiments, the receiving device may be portable. In some embodiments, the receiving device may be placed in the vicinity of the sensing device. In some embodiments, the receiving device may be placed at a remote location, but still in acoustic communication range from the transmitting device. In some exemplary embodiments, the receiving device is a smart phone. In some exemplary embodiments, the receiving device is configured to communicate with a smart phone.

Figure 10:
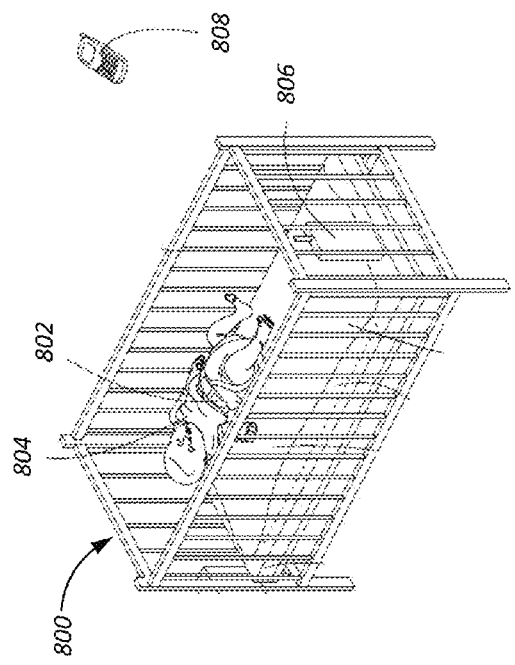
FIG. 10 shows a schematic illustration of an acoustic interface of a sensor system.

Reference is now made to FIG. 10, which shows a schematic illustration of an acoustic interface of a sensing system, according to some embodiments. In a system 800, a sensing device 802 is placed on a subject (exemplary baby 804). When an event is detected by the sensor of the sensing device, an acoustic alert is produced by the sensing device. The acoustic alert is detected by a receiving device such as receiving device 806, which is located in the proximity of the subject. The receiving device may then issue an alert (such as audible, tactile and/or visual alert) to a supervisor. Additionally or alternatively, the receiving device may serve as a relay station configured to communicate with a remote device (such as smart phone 808), which is, in turn, configured to generate an appropriate alarm to the supervisor. In another embodiment, remote device 808 may embed receiving device 806, and no relaying device may be required.

In some embodiments, the receiving device is configured to communicate with the remote device via the Internet and/or via short-range radio, utilizing technologies such as WiFi, Bluetooth, SMS, cellular data communication, push notification protocol, and activate the alarm therein, in order to notify a supervisor which may be located in a remote location. The remote device may execute an application for communicating with the receiving device and to produce audible and/or visual alarm and/or tactile alarms.

Figure 23:
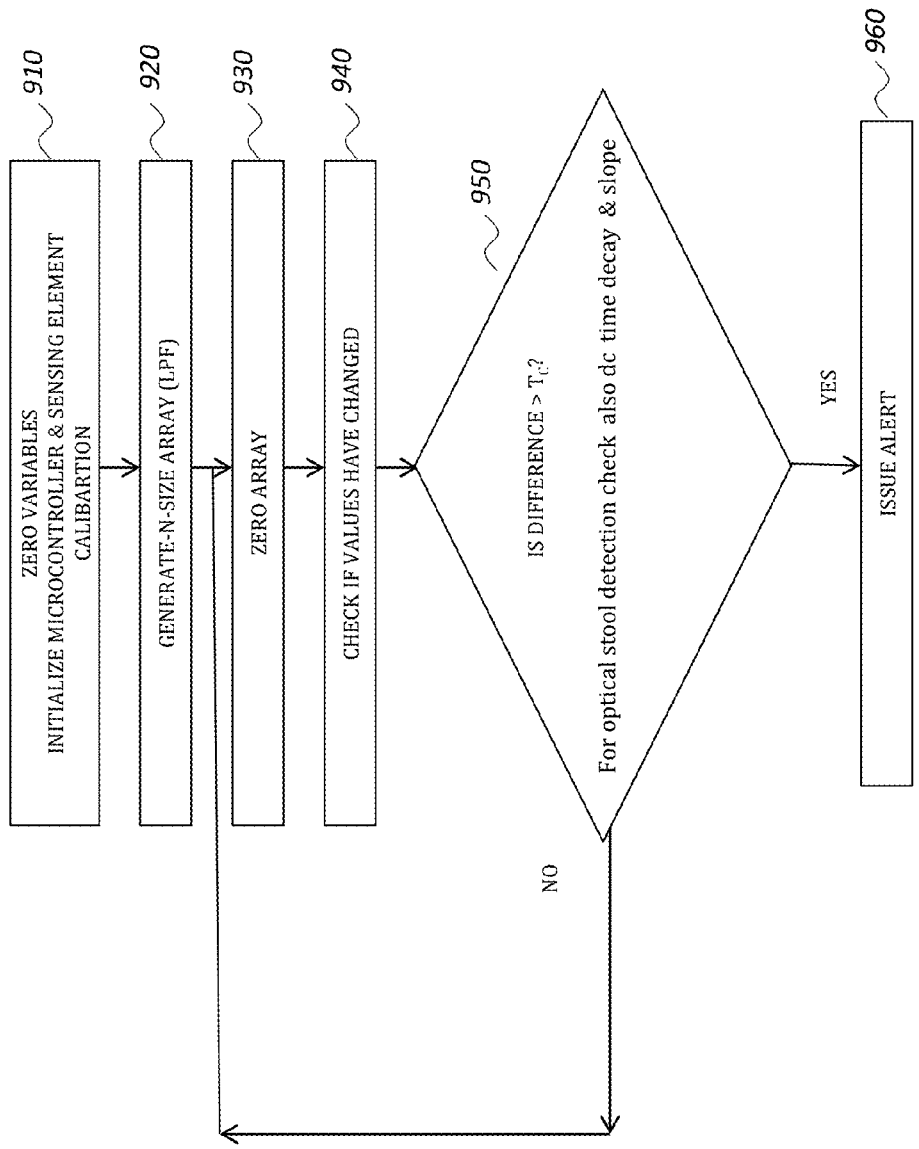
FIG. 23 shows a flowchart of an algorithm for detecting urine and stool secretions.

A flowchart of an algorithm for detecting urine and stool secretions is shown in FIG. 23. Such an algorithm may be implemented as a software routine. In a first step 910, variables are zeroed and the microcontroller is initialized. At least one measurement is performed for calibration purposes. This measurement is used as a baseline value for further measurements. In step 920, an N-sized array for storing the last N consecutive sensor readings is generated. In step 930 the N-sized array is zeroed. The N-sized array may include a number of cells corresponding, for examples, to a few seconds or a few dozen seconds based on the sampling rate of the sensor. In step 940, a difference between the N consecutive sensor readings is calculated. The calculation may include a process for noise filtering. In step 950, it is checked if the difference exceeds a pre-set threshold $T_C$, which is pre-programmed in the integrated circuit. If the threshold is exceeded, then the algorithm continues to step 960 and an alert is issued. If the threshold is not exceeded, then the routine returns to step 930 in which zeroing of the array is performed.

In addition for the optically methods of stool detection, before checking the $T_C$, the DC time decay & slope are measured for pre-set threshold.

$T_C$ may be pre-set to match a specific type of diapers which have the same material characteristics, (e.g., in regard to their light reflection or capacitive behavior), when the diaper is dry and when urine and/or stool are present. The pre-setting may be performed during manufacturing, based on tests run on the pertinent type of diaper.

Alternatively, $T_C$ may be set dynamically each time it is coupled with a new diaper. A calibration phase occurs in step 910 may be employed each time the sensor is turned on and/or coupled with a diaper. In such a calibration phase, the initial average value received from the detector is stored for later use as a baseline, namely—$T_C$.

Experimental Results

Multiple experiments have been conducted in order to establish the efficacy of present embodiments, and show their supremacy over other configurations.

In a first experiment (also referred as experiment no. 1), a capacitive sensor (P/N:HCH-1000-001 made by Honeywell) was positioned on the outer side of an infant diaper on a lab table. The output leads of the sensor was connected to a capacitance measuring instrument.

Figure 24:
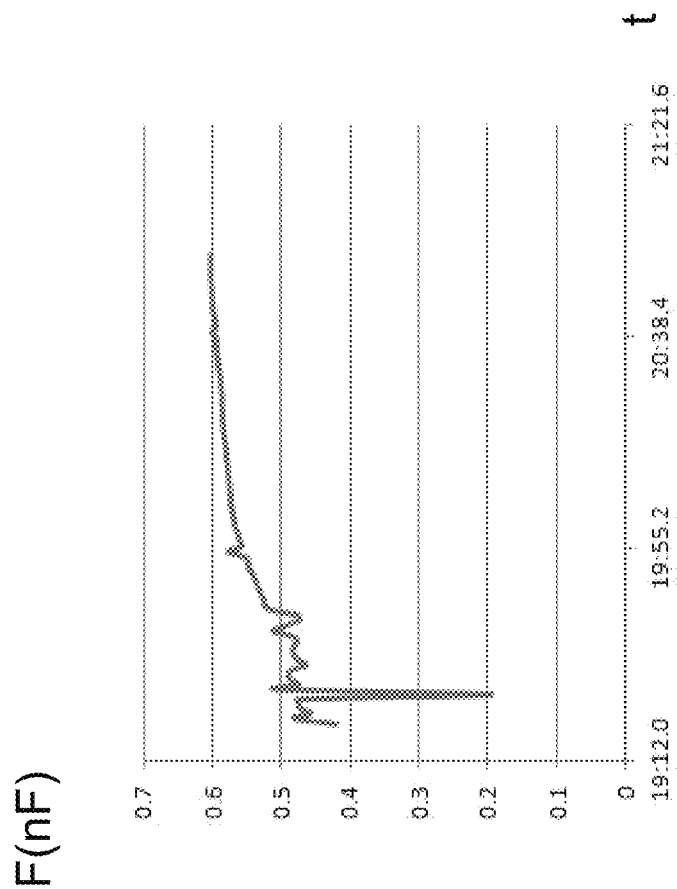
FIG. 24 shows a graph of output capacitance vs. time of a capacitive sensor mounted on an infant diaper during a period of time in which the diaper was soiled with urine.

Reference is now made to FIG. 24 which shows graph of output capacitance vs. time of a the capacitive sensor. A 30 cc of urine was poured into the backside of the diaper. during a period of time in which the diaper was soiled the capacitance was increased from 0.47 nF to 0.60 nF, Therefore an obvious change of capacitance was observed from t=0 to steady state, after poured the urine into the diaper.

Figure 11A:
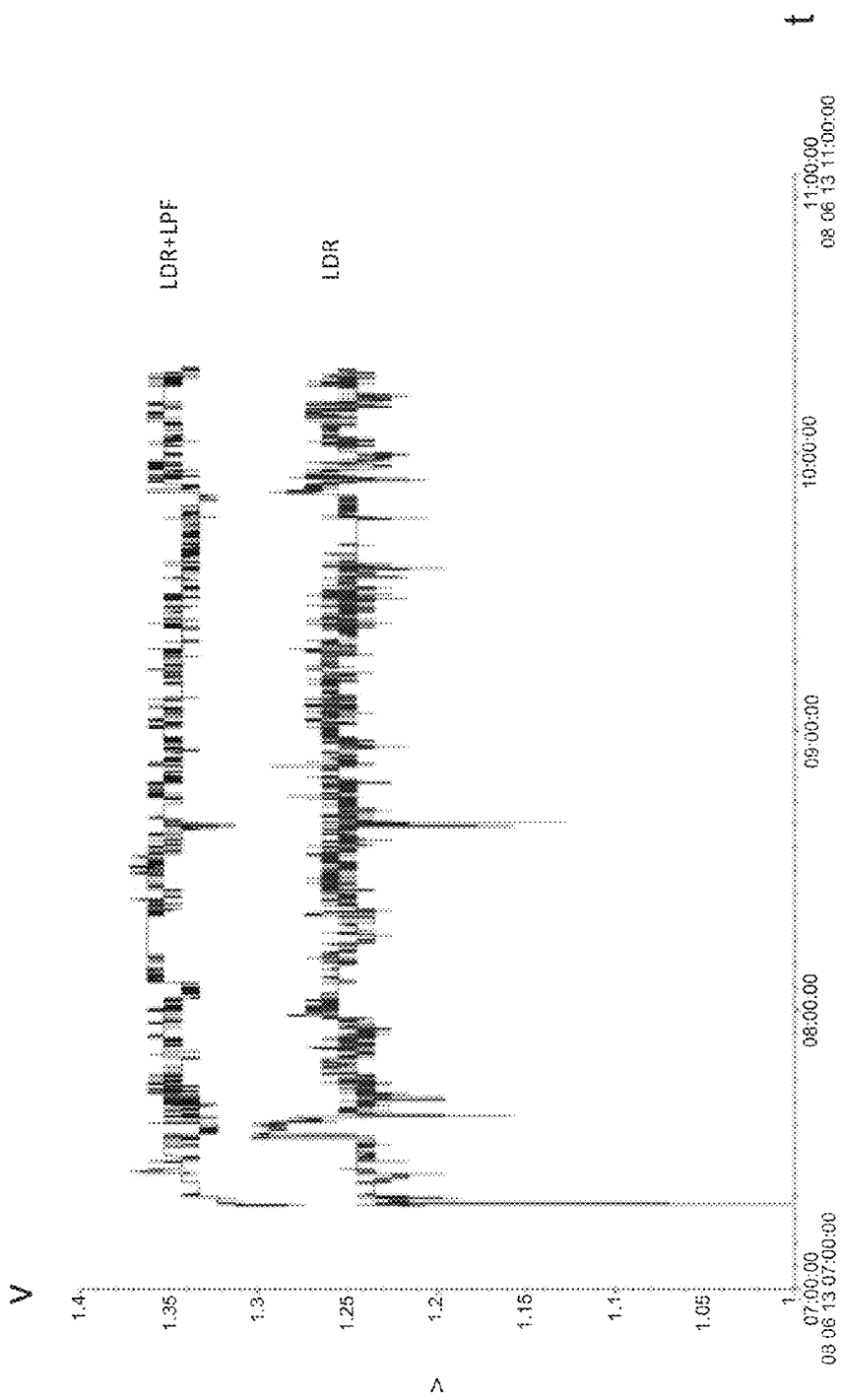
FIG. 11A shows graphs of output voltage vs. time of a sensor configuration including a control LDR and an LDR joint with an LPF positioned on an infant during a first period of time in which no secretion was found.
Figure 11B:
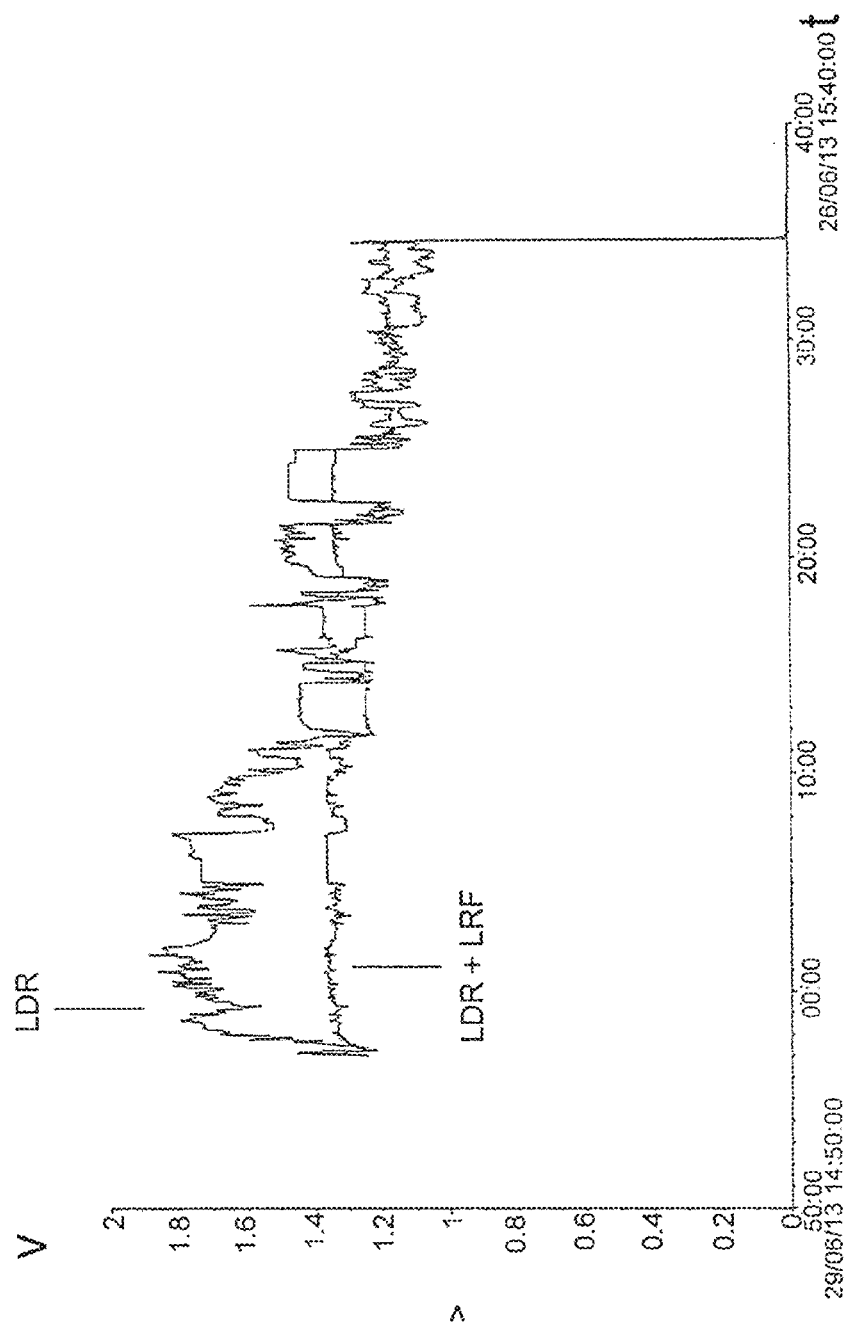
FIG. 11B shows graphs of output voltage vs. time of the sensor configuration of FIG. 11A during a second period of time in which the infant defecated.
Figure 11C:
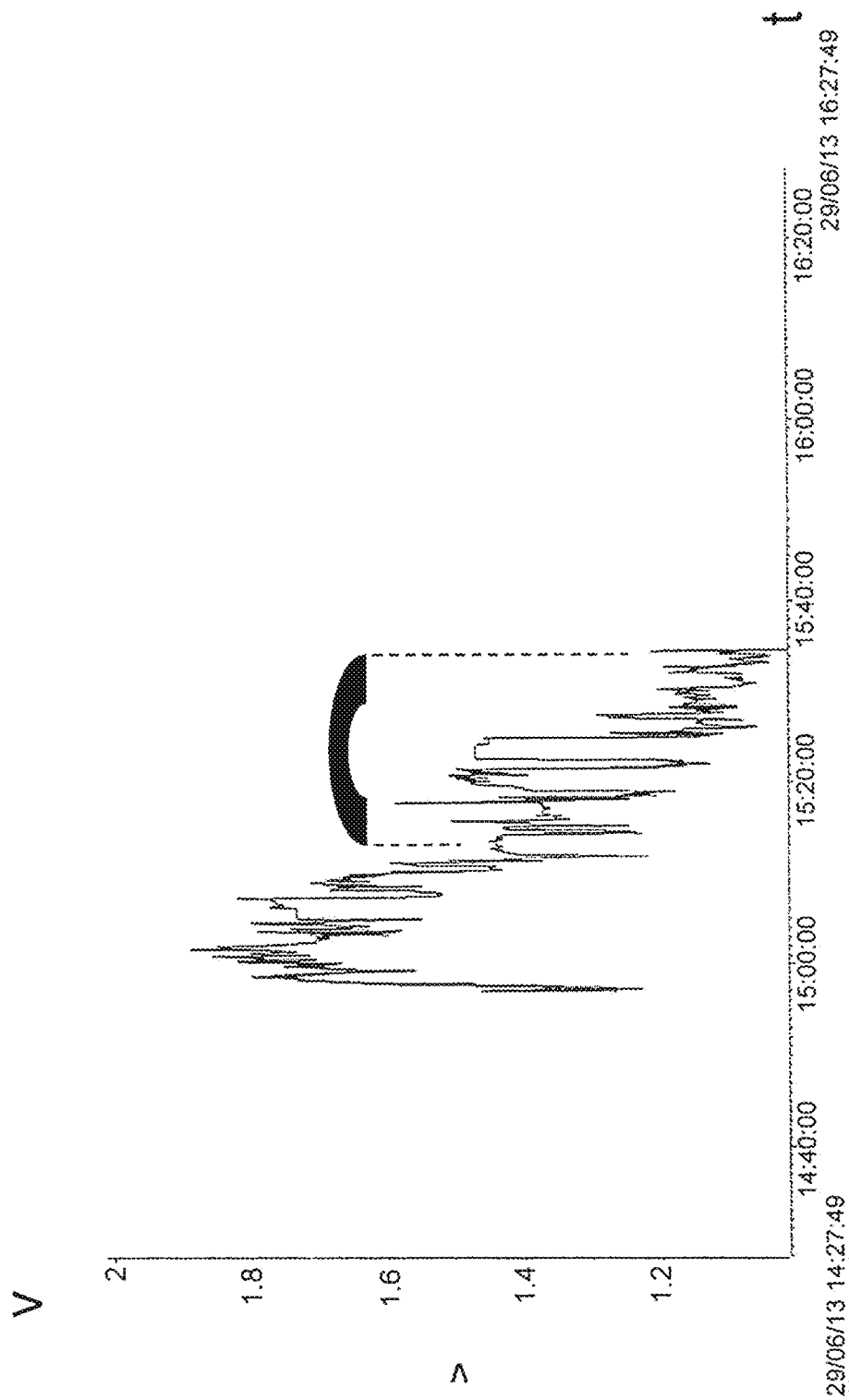
FIG. 11C shows the output voltage of the LDR of the sensor configuration of FIG. 11B in a separate manner.
Figure 12A:
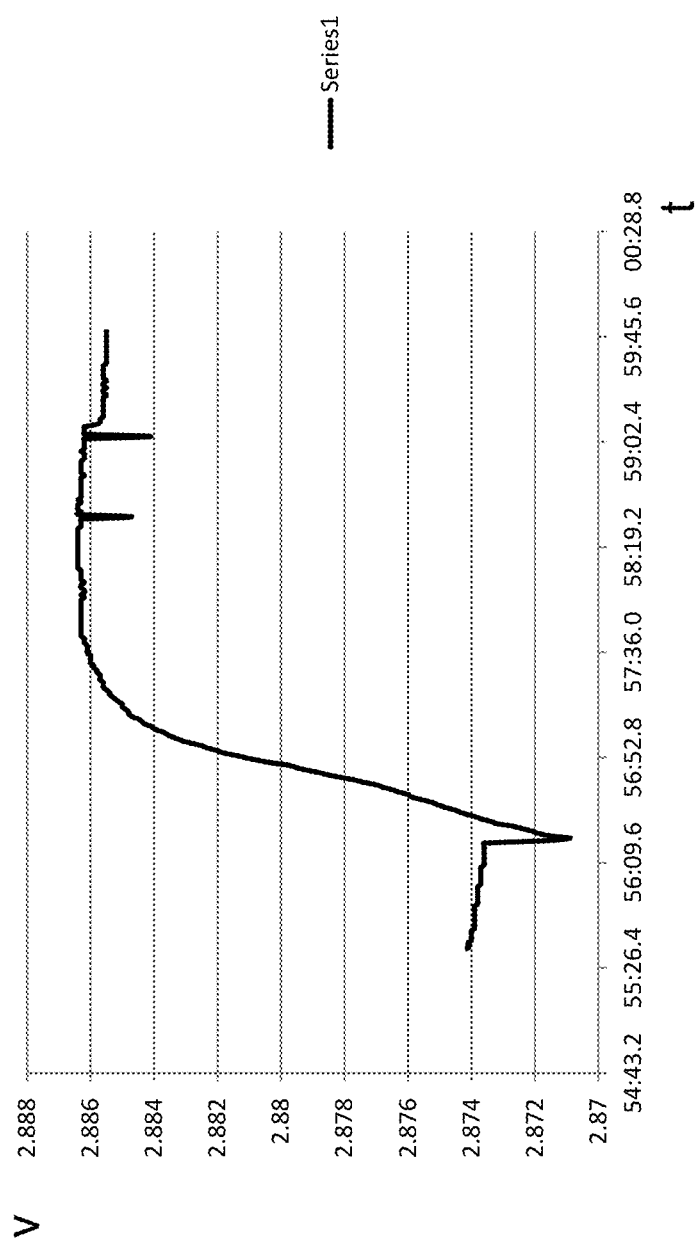
FIG. 12A to 12E show graphs of a LDR output voltage vs. time as a result of a red LED illumination on red, white, black, green and blue garments correspondingly.
Figure 12B:
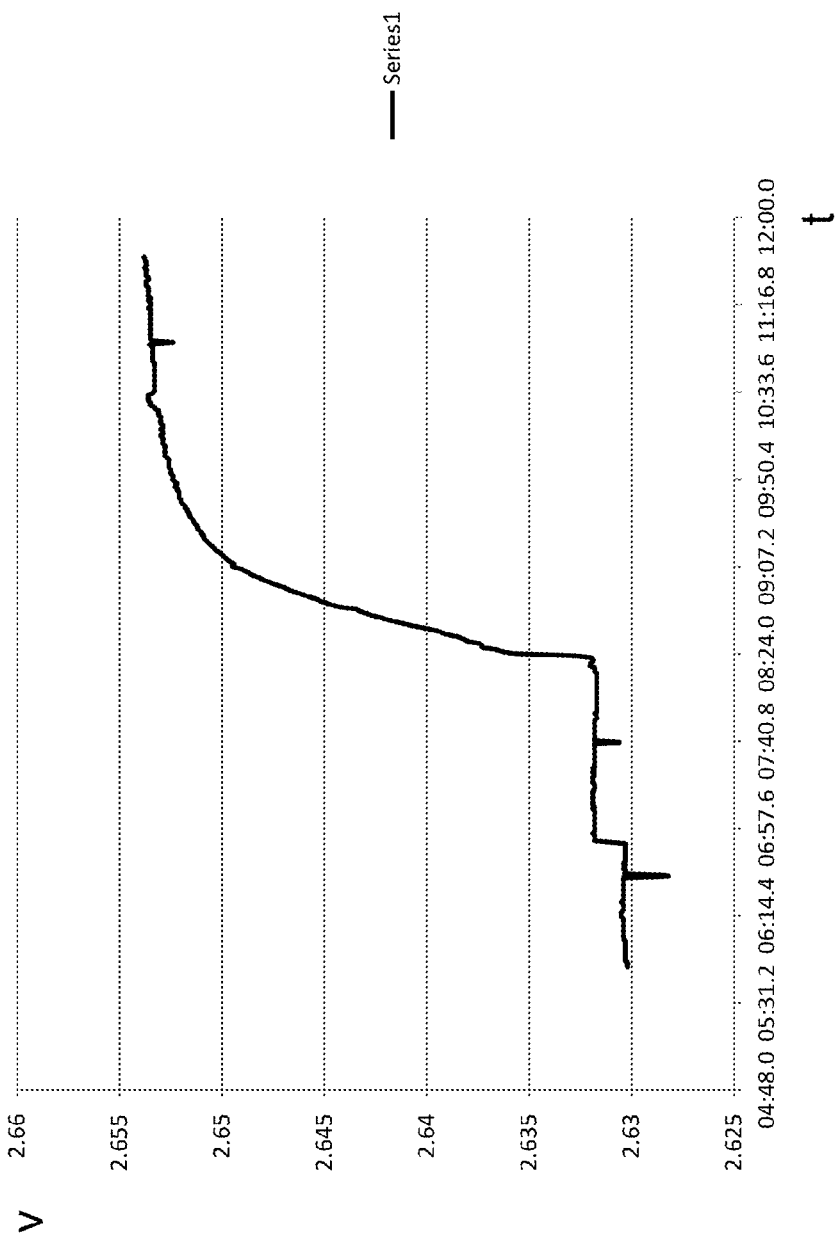
Figure 12C:
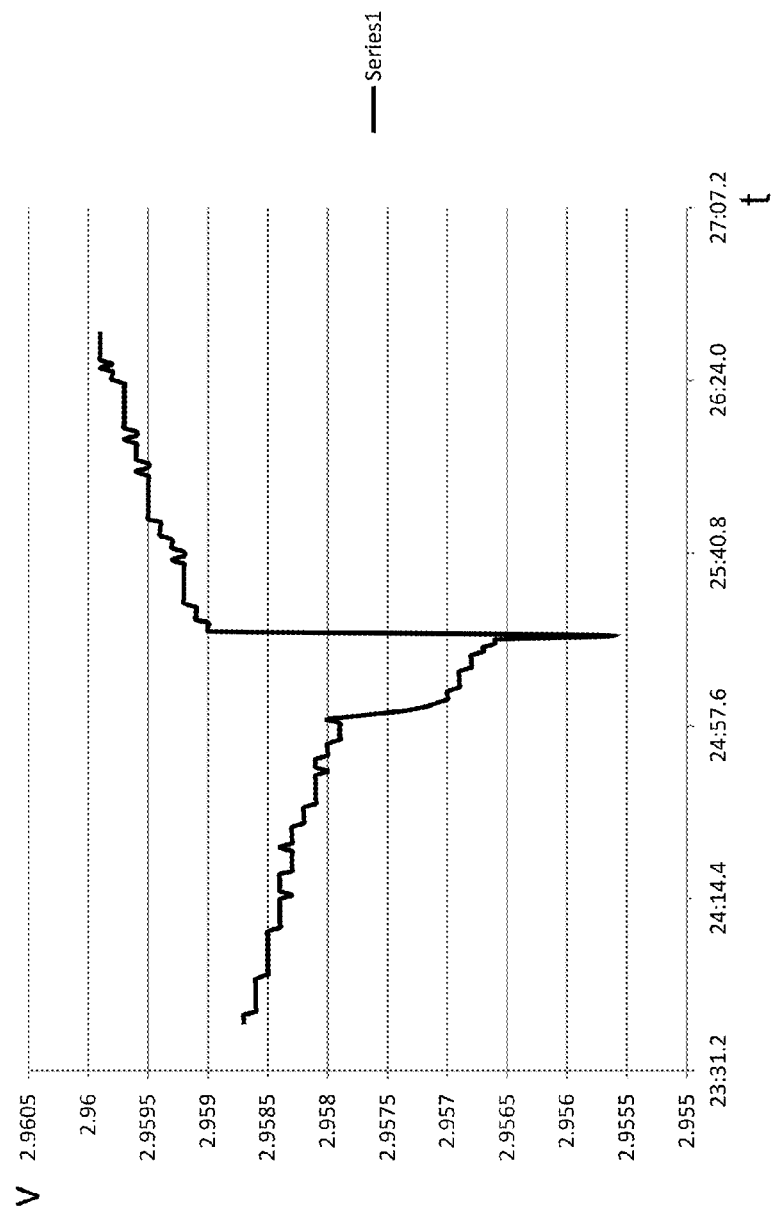
Figure 12D:
Figure 12E:
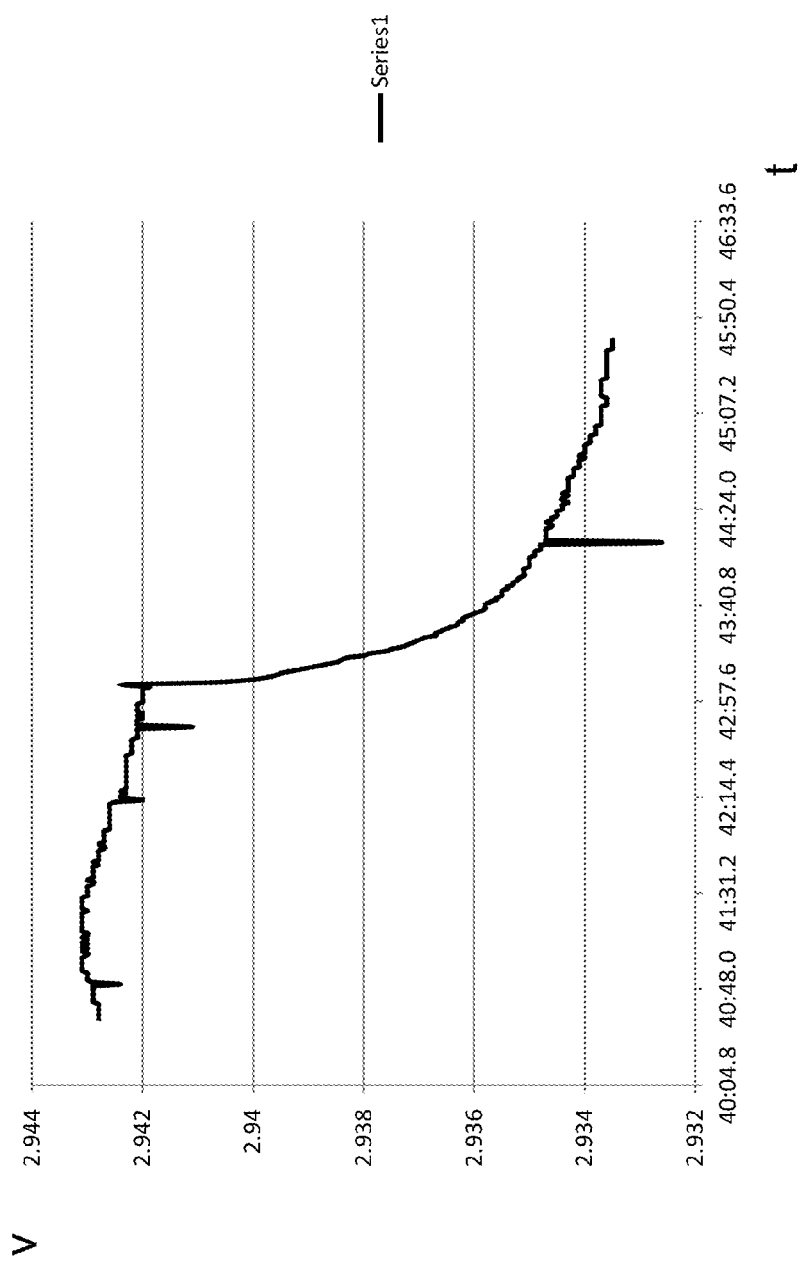
Figure 13A:
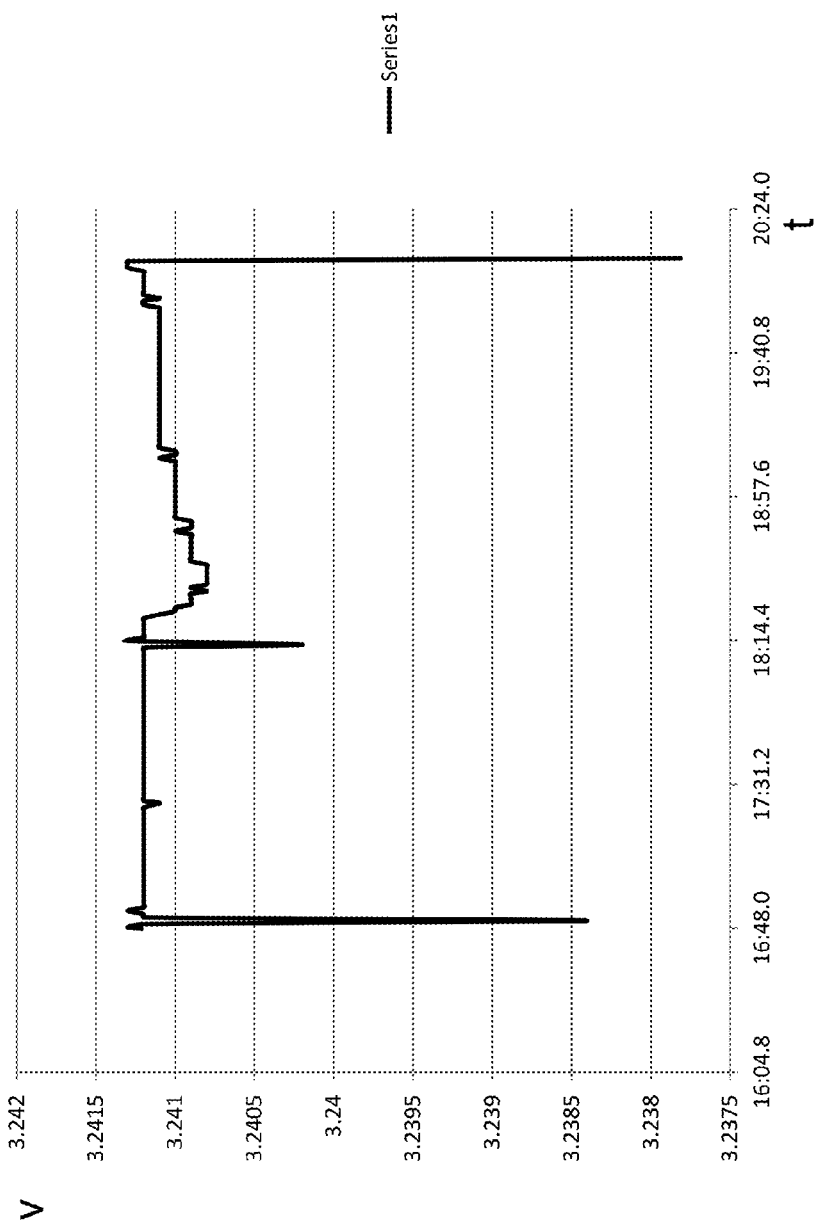
FIG. 13A to 13E show graphs of a LDR output voltage vs. time as a result of a green LED illumination on blue, white, black, green and red garments correspondingly.
Figure 13B:
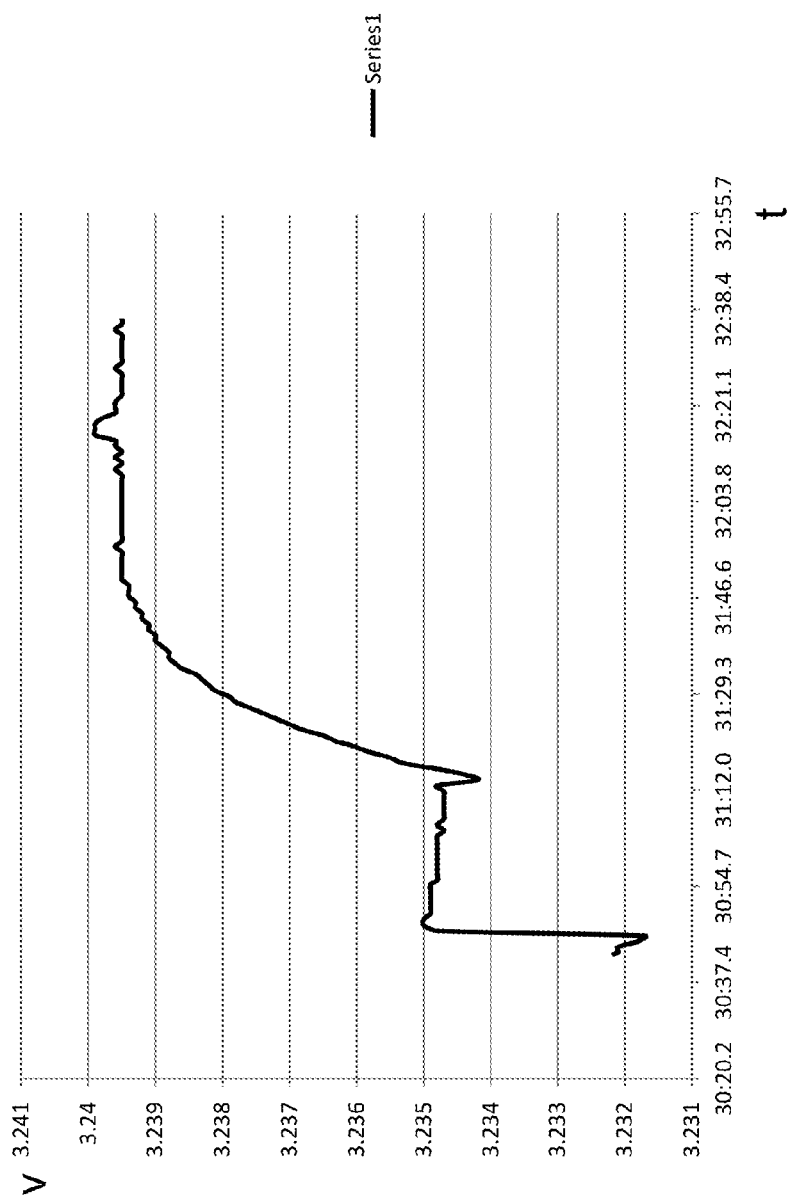
Figure 13C:
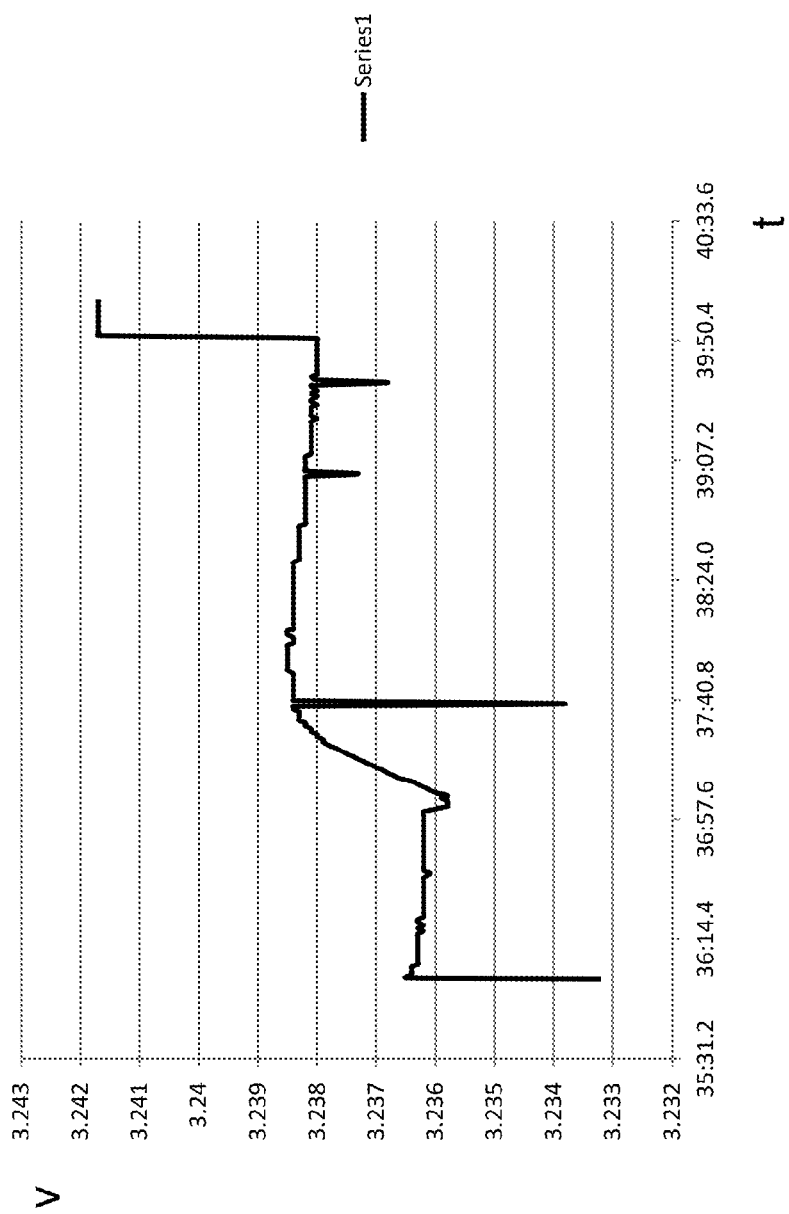
Figure 13D:
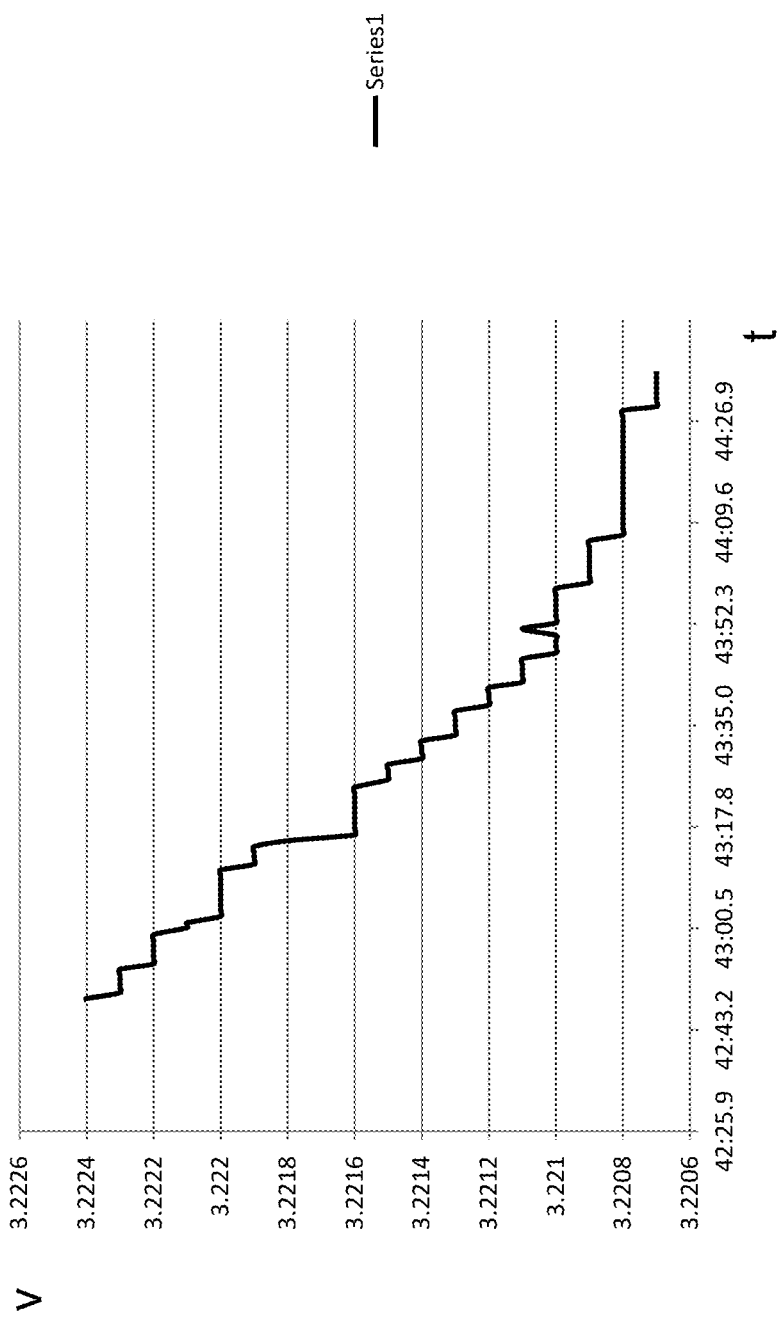
Figure 13E:
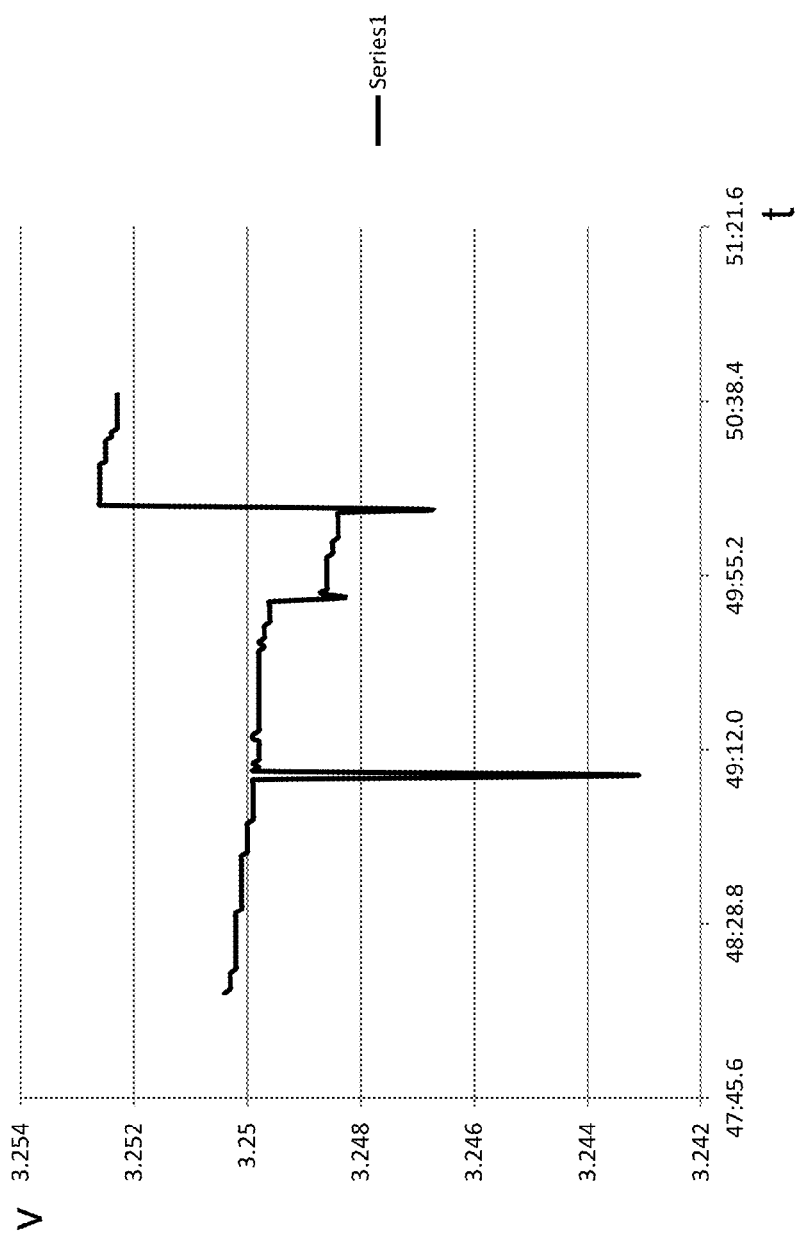
Figure 14A:
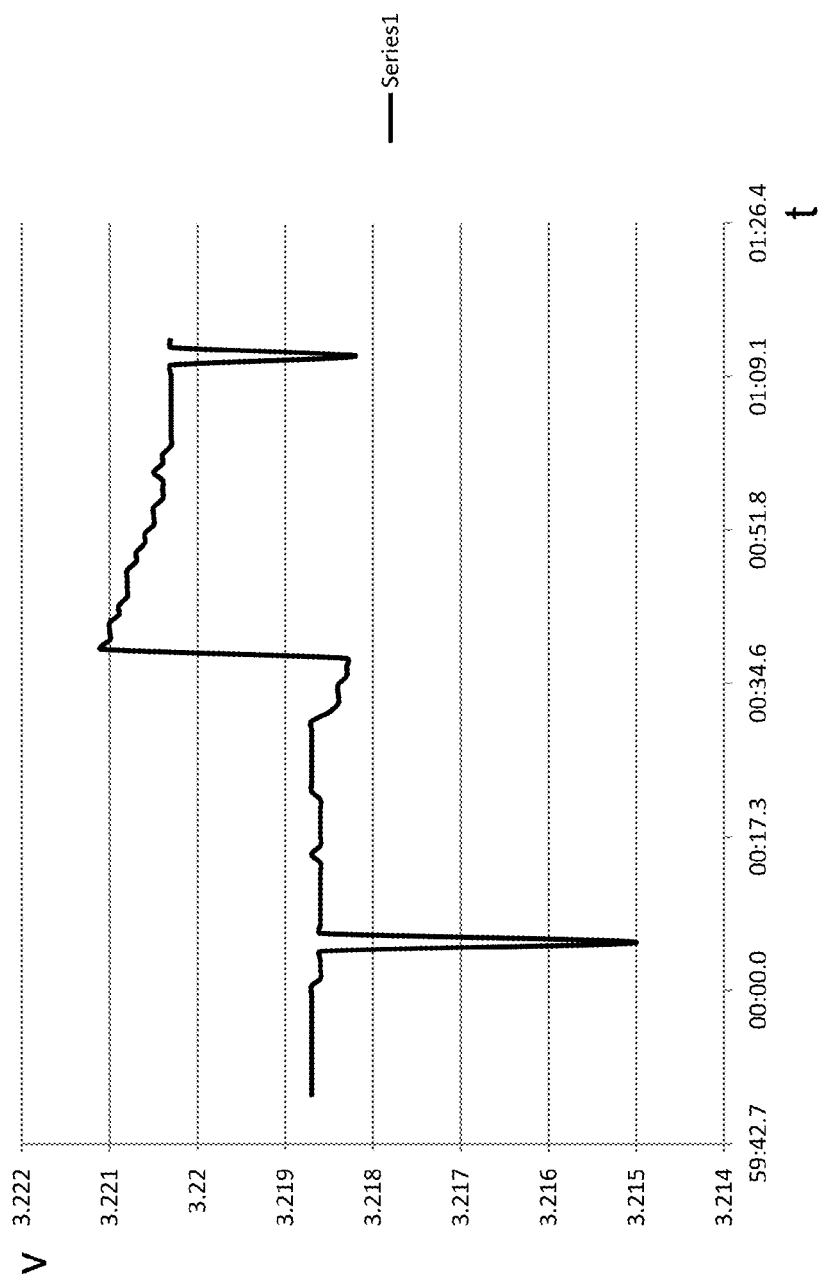
FIG. 14A to 14E show graphs of a LDR output voltage vs. time as a result of a blue LED illumination on red, white, black, green and blue garments correspondingly.
Figure 14B:
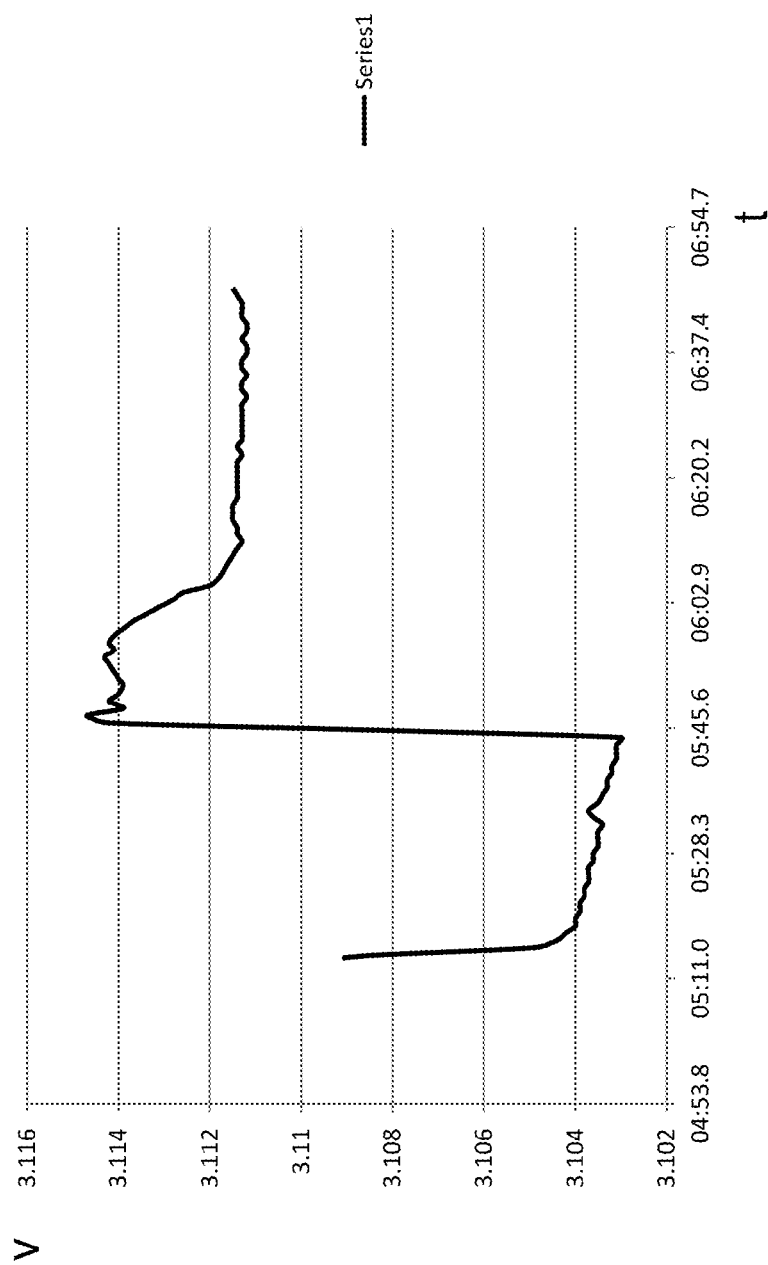
Figure 14C:
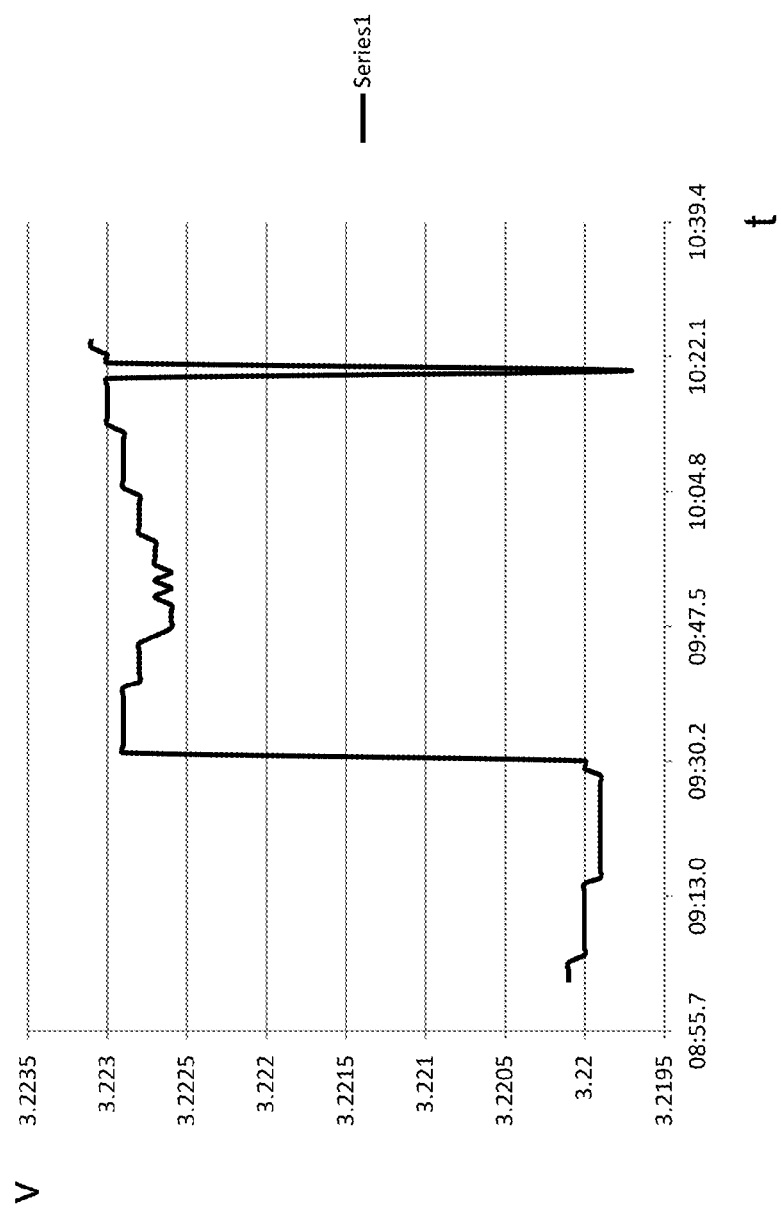
Figure 14D:
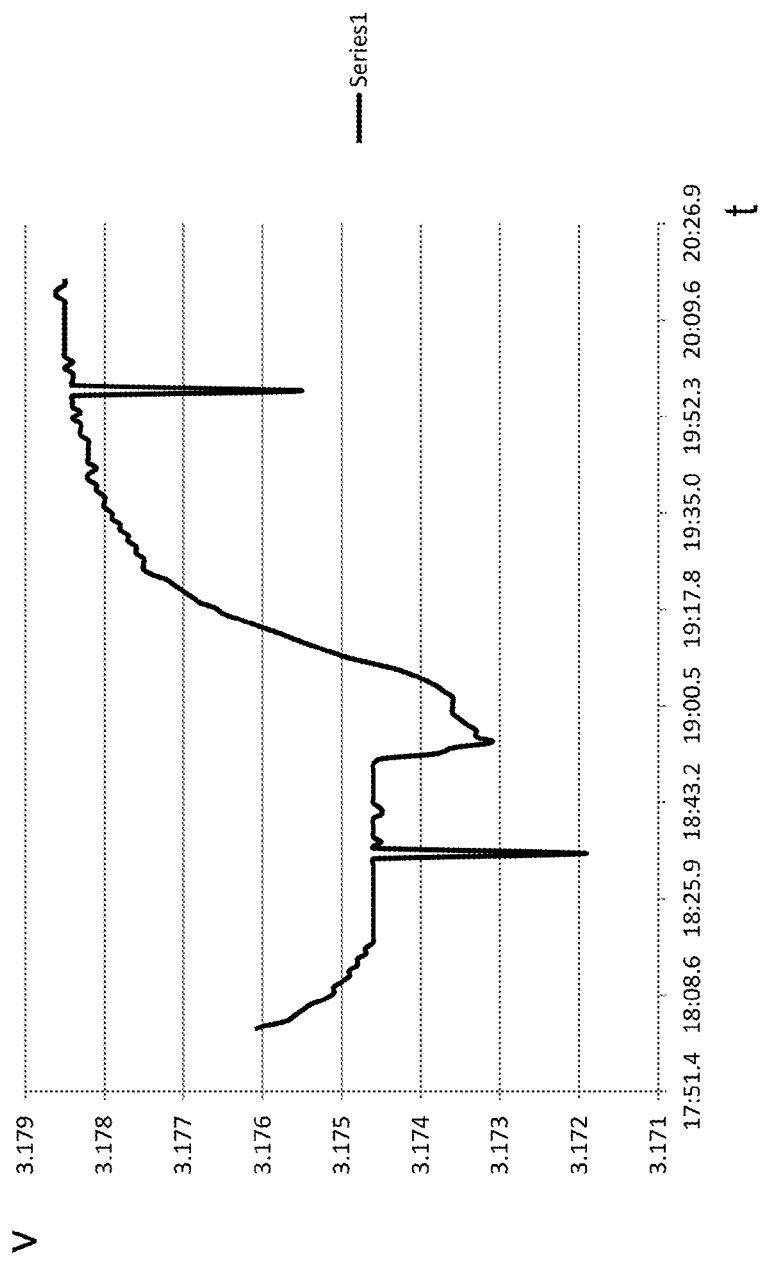
Figure 14E:
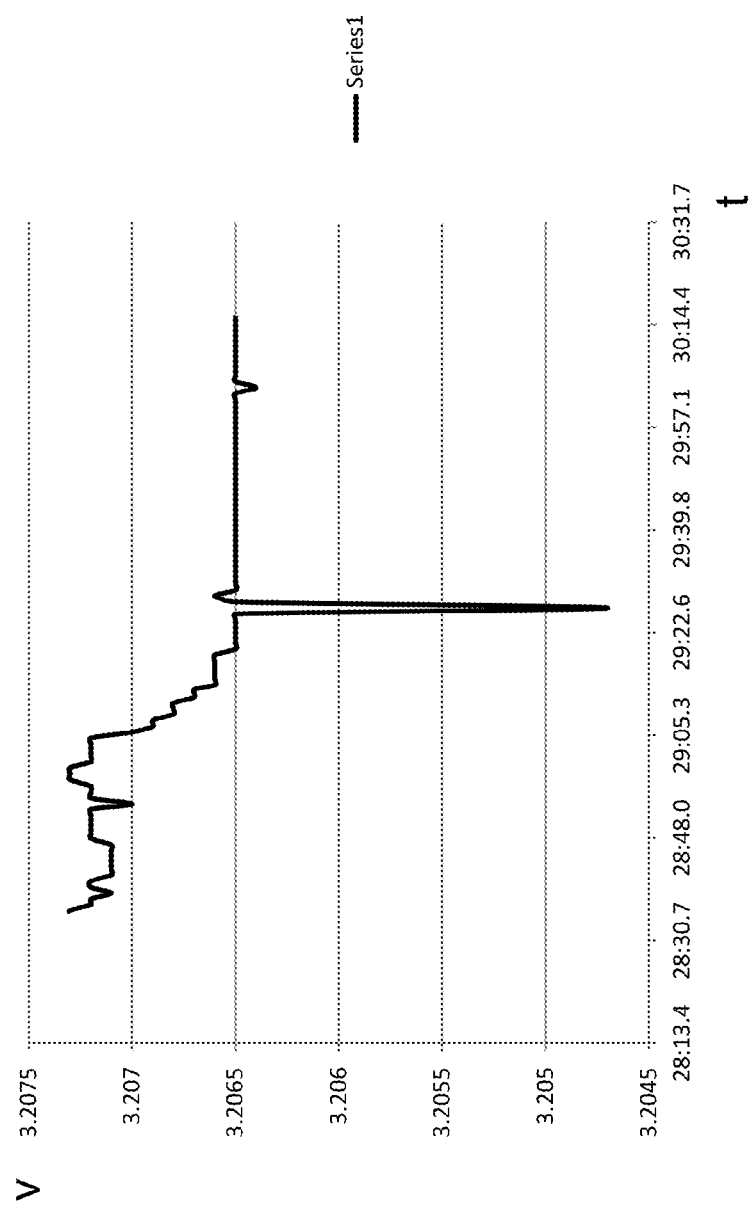
Figure 15A:
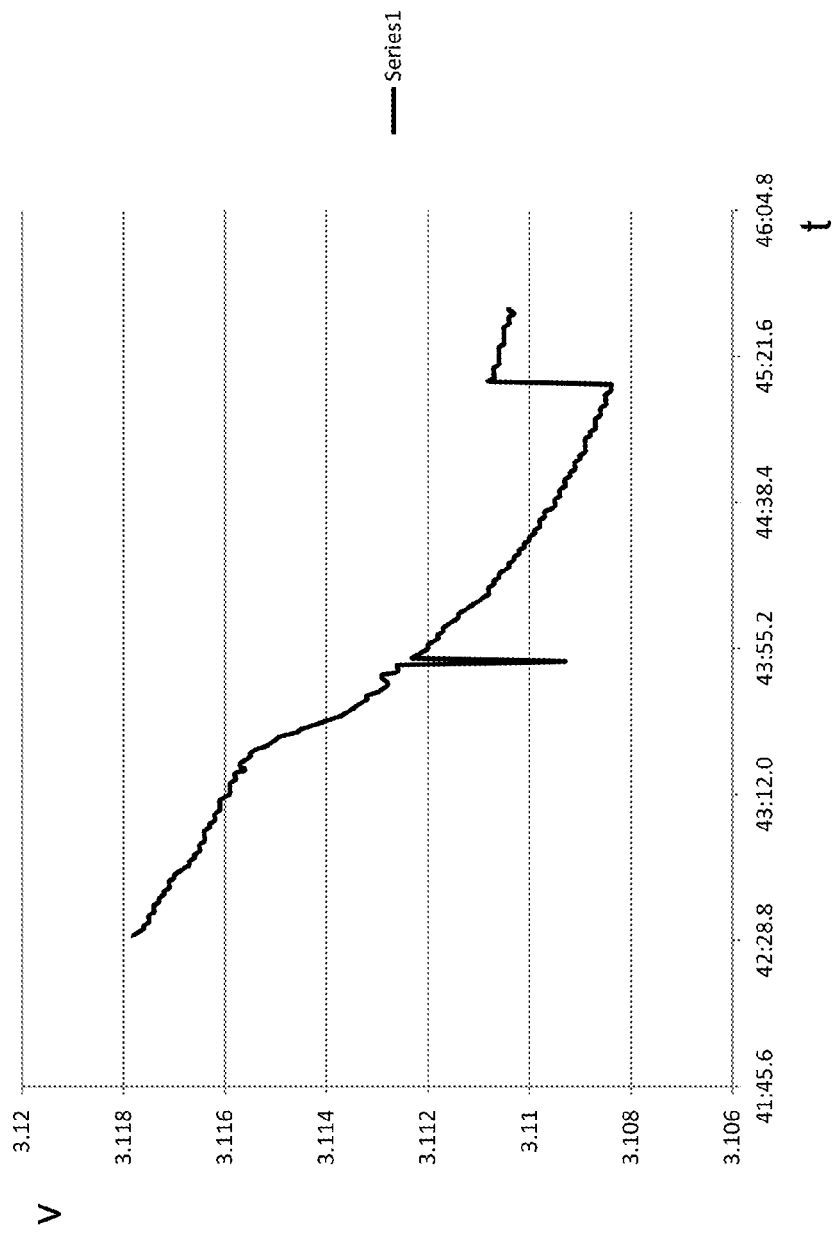
FIG. 15A to 15E show graphs of a LDR output voltage vs. time as a result of a white LED illumination on red, white, black, green and blue garments correspondingly.
Figure 15B:
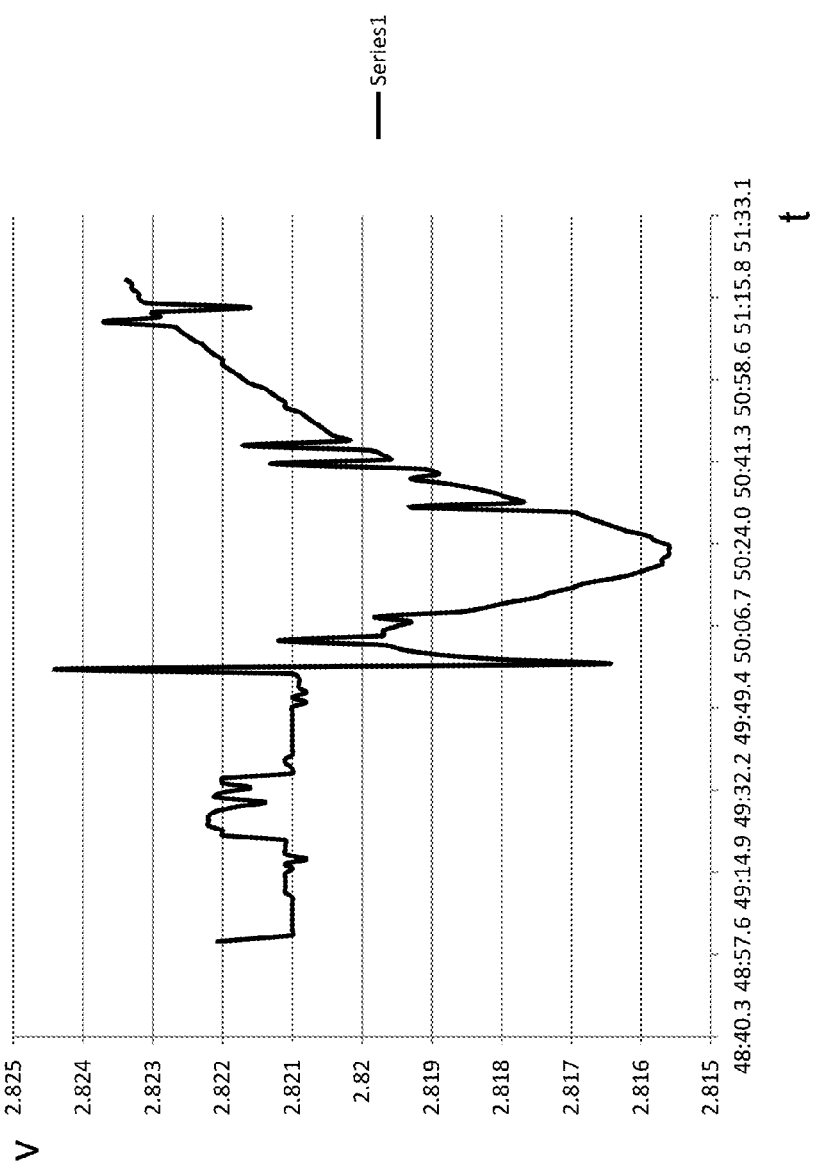
Figure 15C:
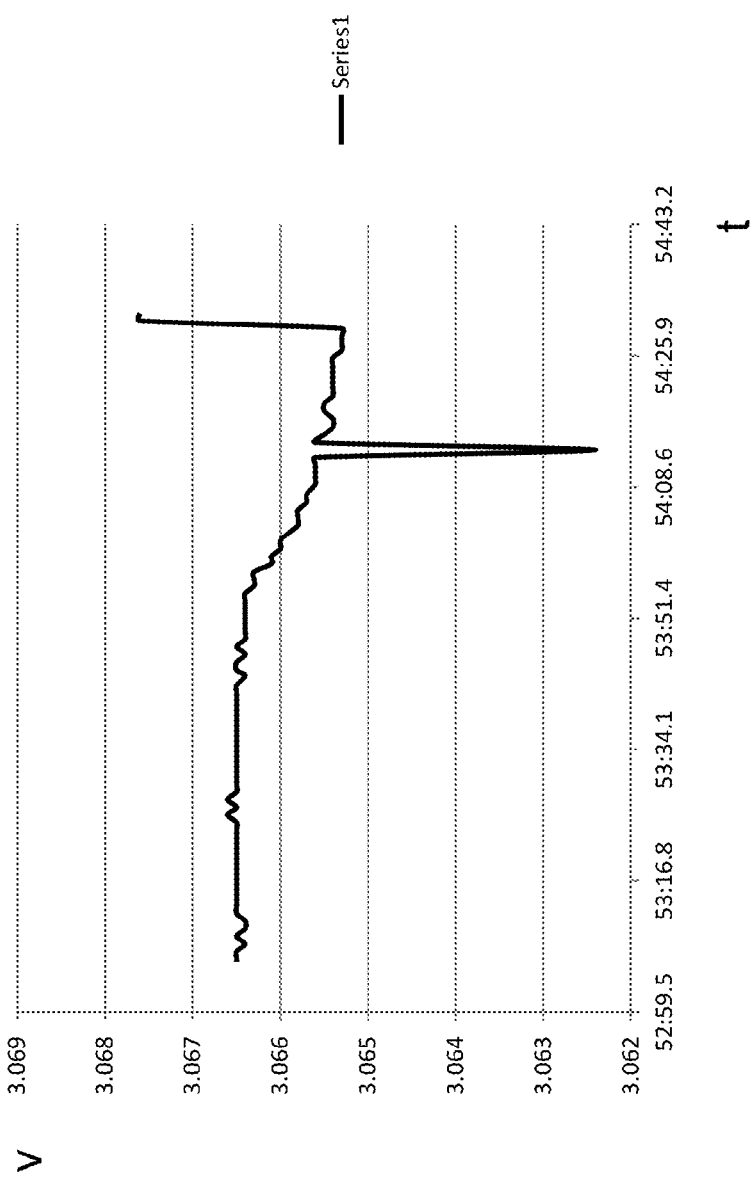
Figure 15D:
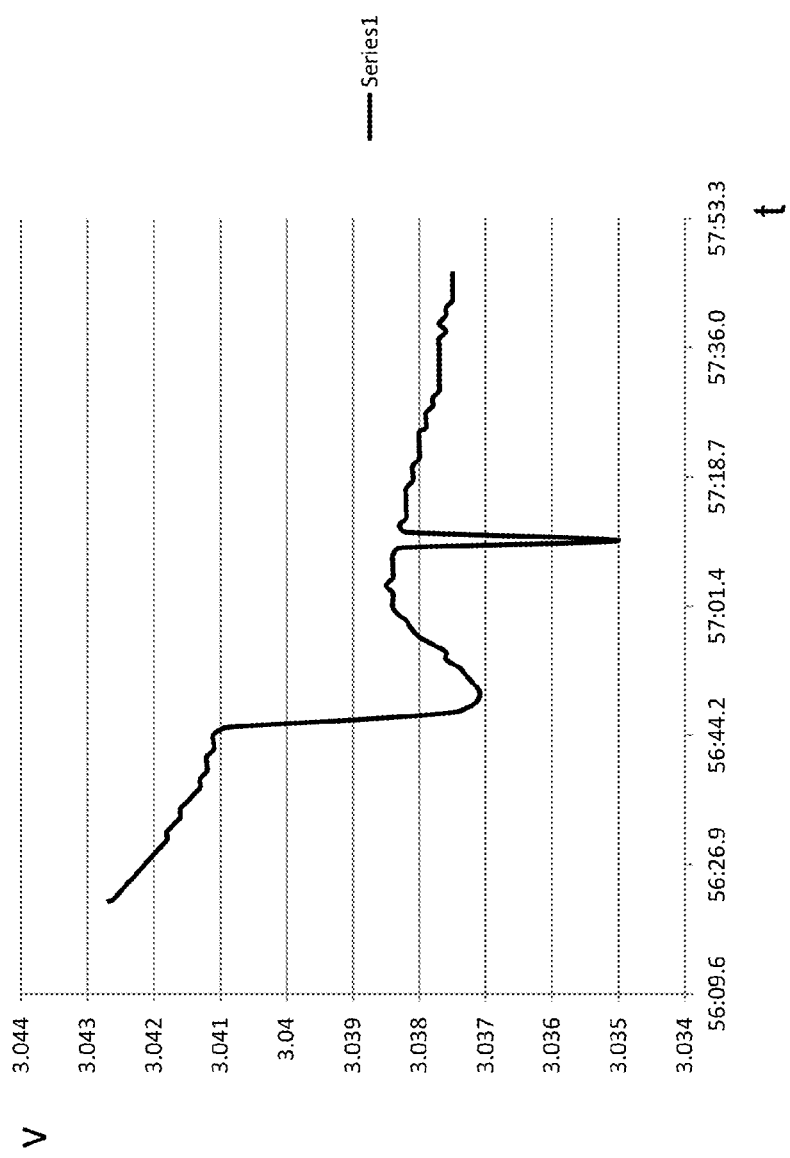
Figure 15E:
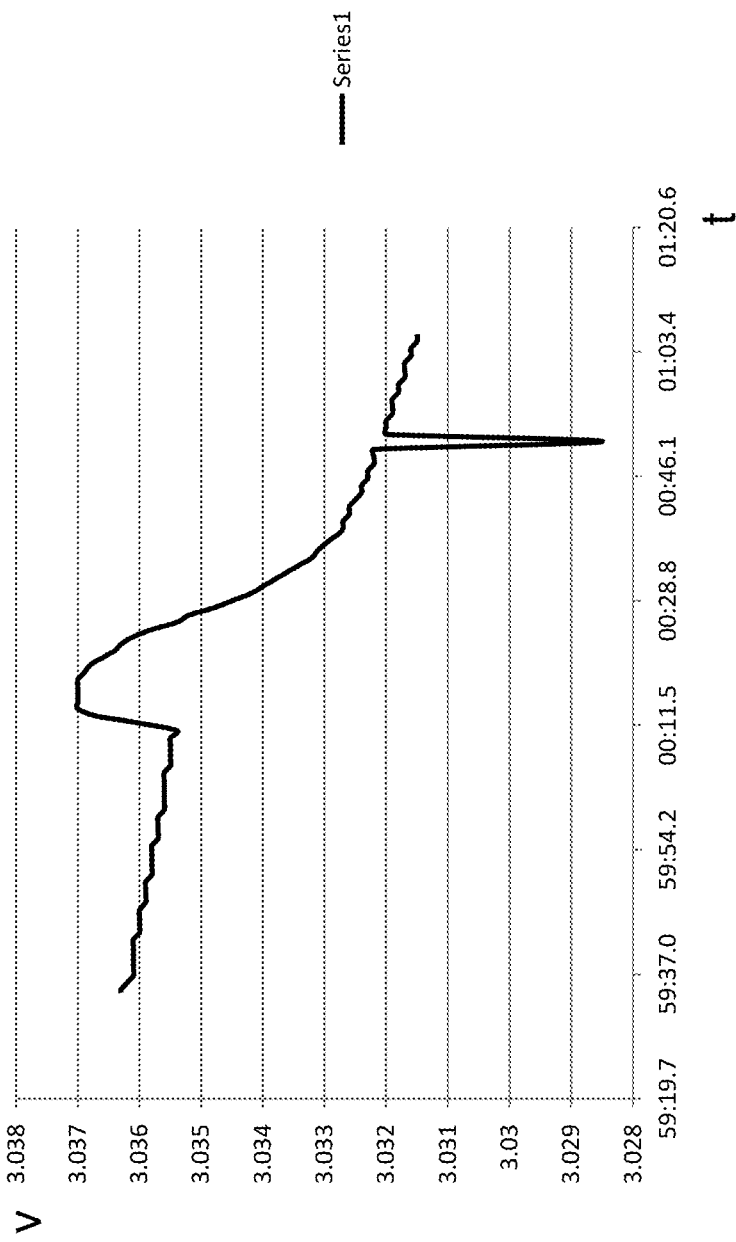
Figure 16A:
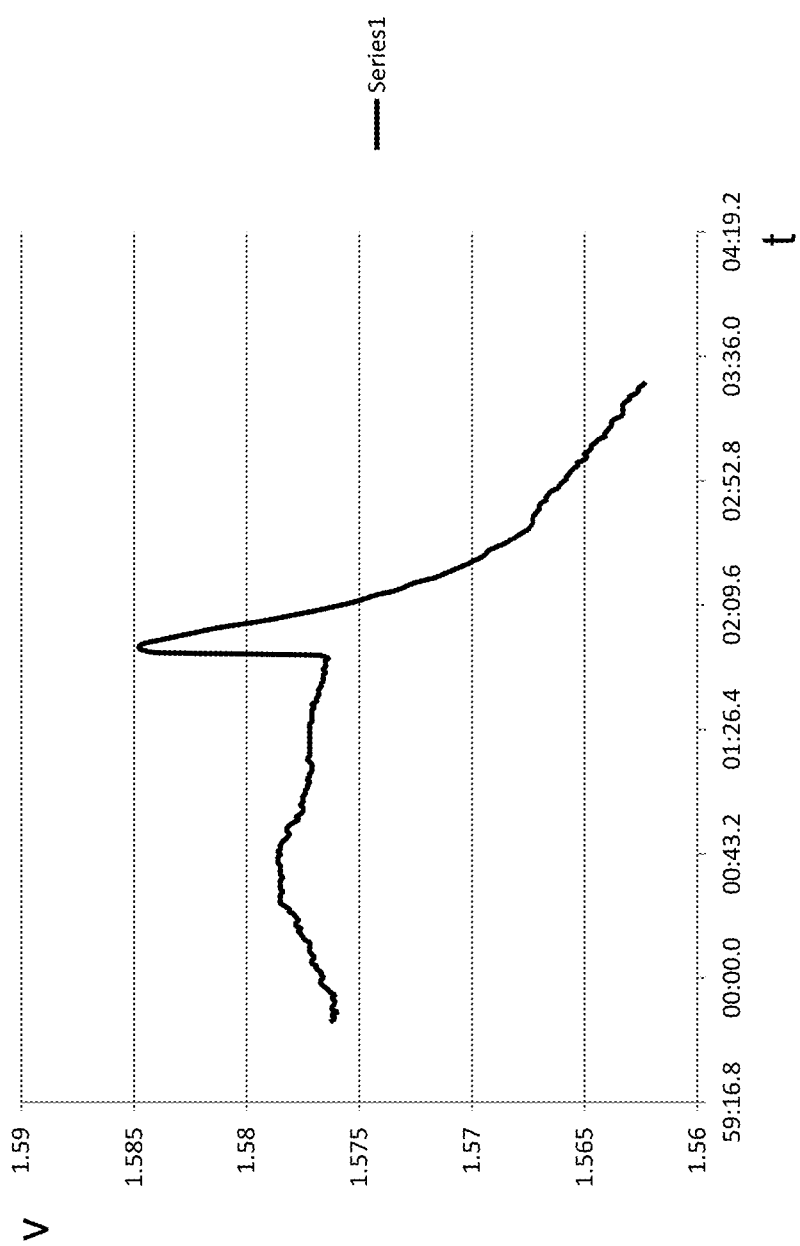
FIG. 16A to 16E show graphs of an IR photodetector output voltage vs. time as a result of a red LED illumination on red, white, black, green and blue garments correspondingly.
Figure 16B:
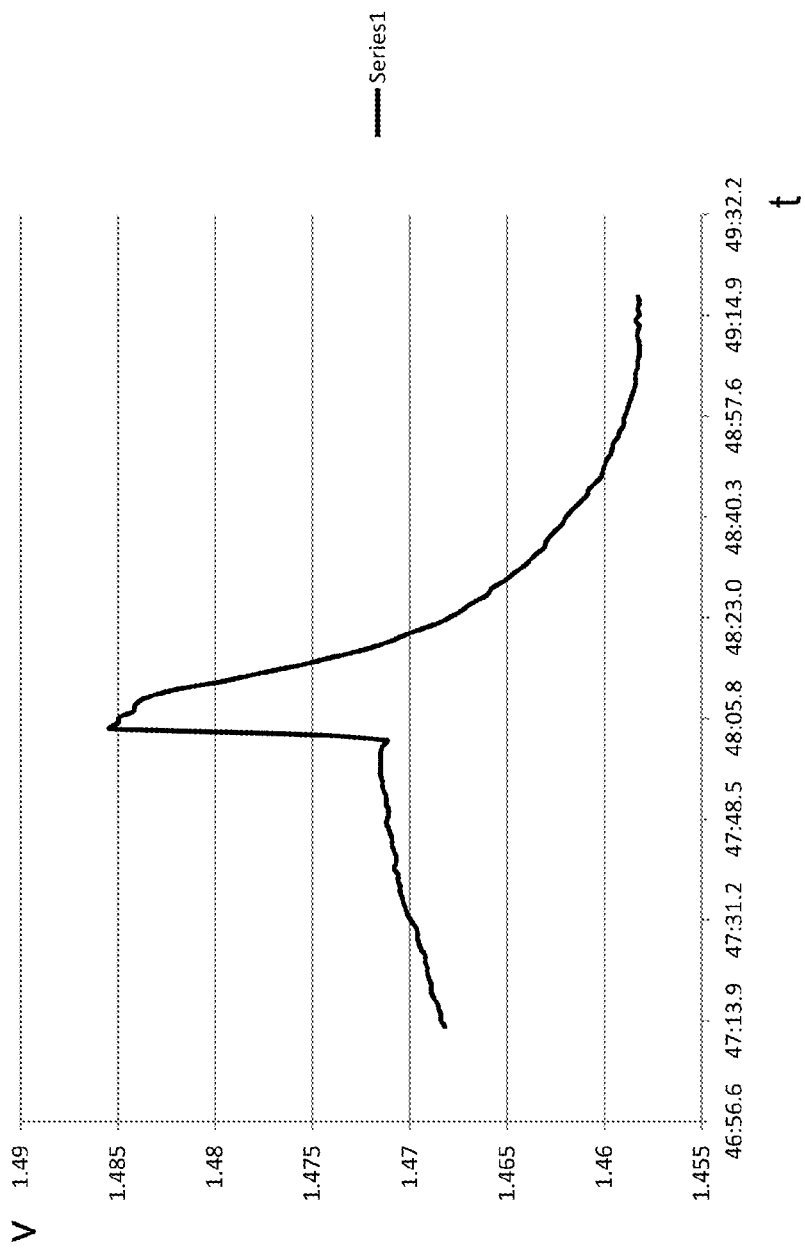
Figure 16C:
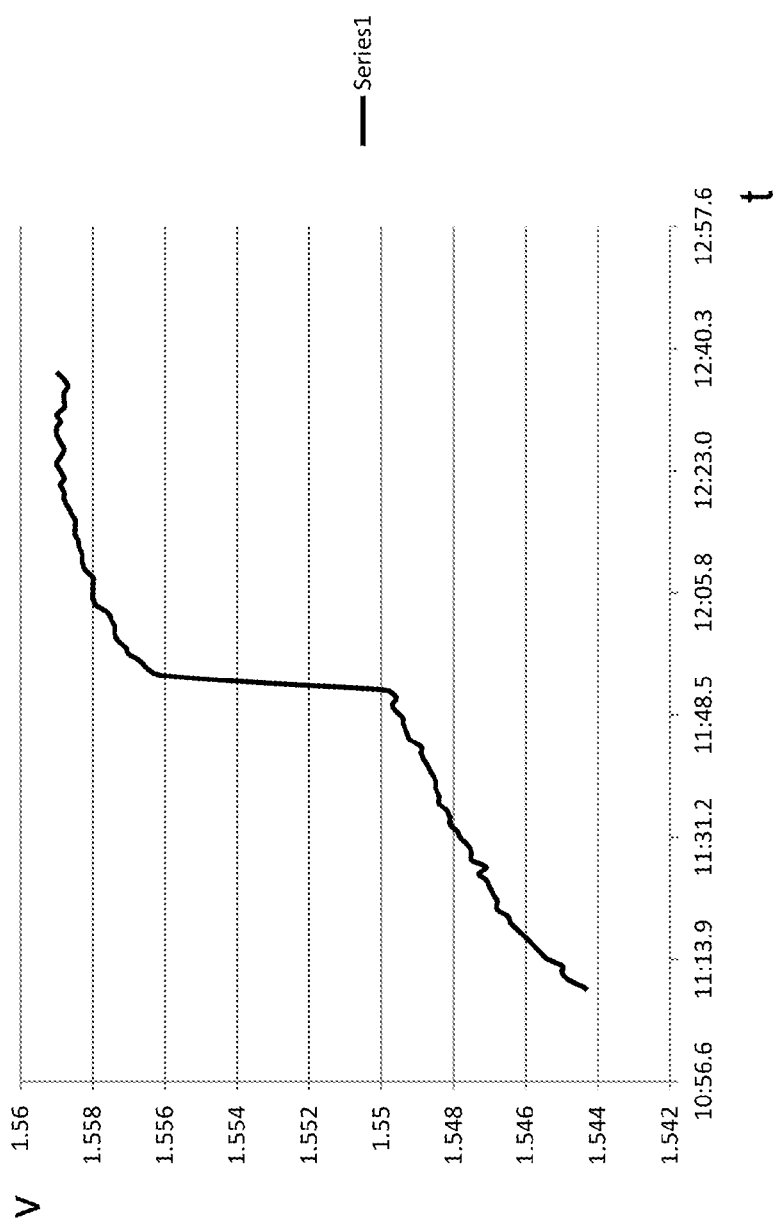
Figure 16D:
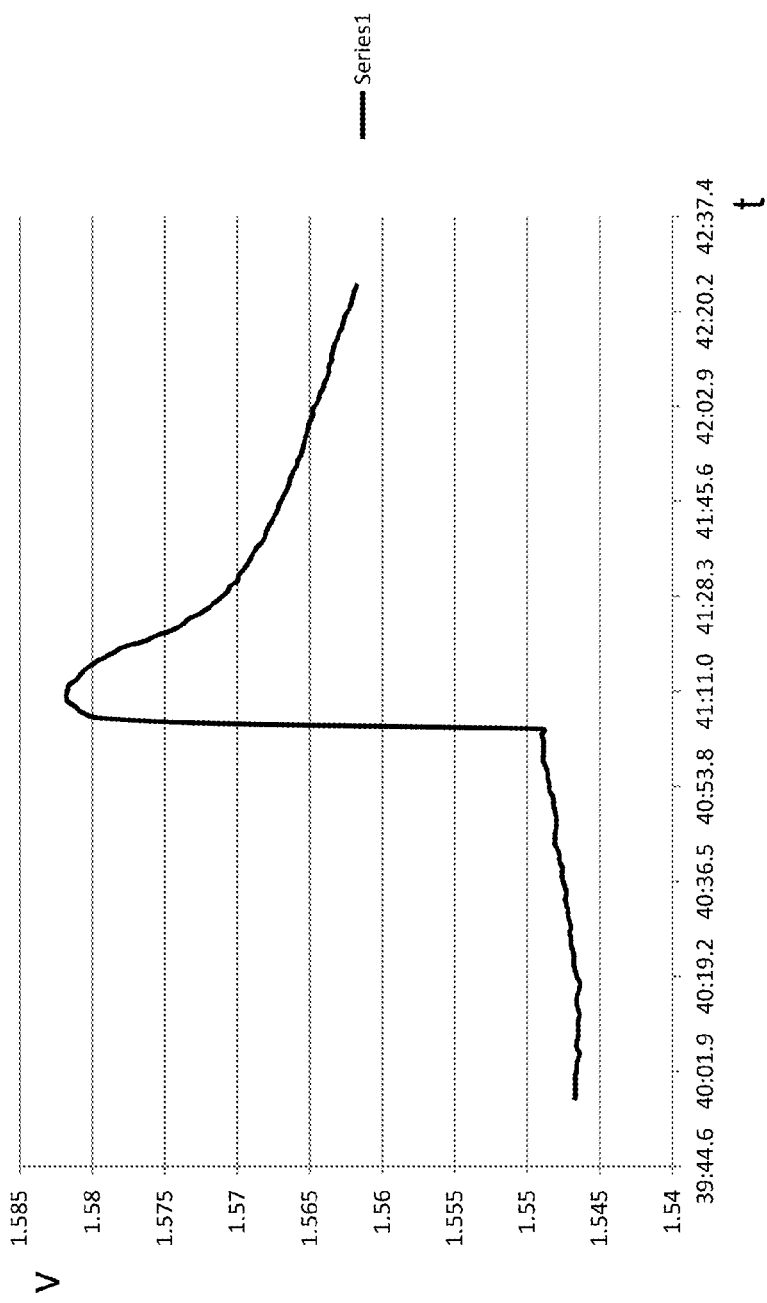
Figure 16E:
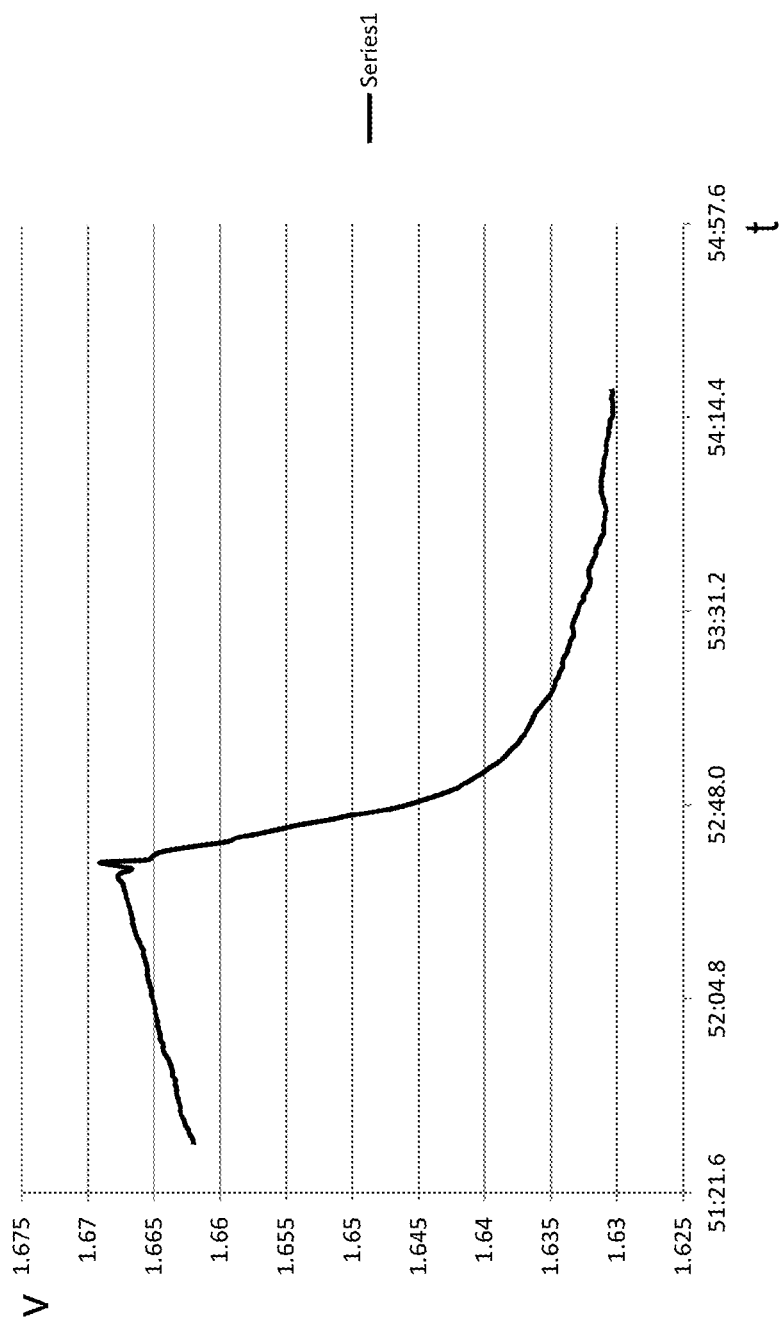

In a second experiment (also referred as experiment no. 2), two LDRs (Light Dependent Resistor) (P/N:PDV5001 made by Advanced Photonix) and a 645 nm red LED (P/N:HT-191URO made by Harvatek) have been used. In a first configuration, both LDRs were positioned, on the bottom of the front part of a diaper put on an infant for better detection of stool. One LDR was equipped with a Low Pass Filter (LPF) including a capacitor of 1 μF and resistor of 10 KΩ (made by AVX Coprporation) in order to diminish noise. As one can see, the graphs have fluctuations, probably due to the infant's movements but the first one the fluctuations is lower because of the LPF. Therefore a noise filter is desired. In this experiment no defecation was observed, accordingly, the output voltage of both LDRs is quite similar. In a second configuration, which was the same as the first configuration. At some point in time the infant defecated and stool was found in the diaper. The results can be seen in FIGS. 11A to 11C, which show graphs of the LDRs output voltage vs. time. During a first period of time, shown in FIG. 11A, no secretion was found. Accordingly, the output voltage of both LDRs is quite similar. During a second period of time, shown in FIG. 11B, the infant defecated and stool was found in the diaper. Reference is now made to FIG. 11C which show the output voltage of the LDR without LPF as shown in FIG. 11B. One can see that at the relevant time (i.e., time of defecation), a difference of 350 mV is shown in the output voltage of the LDR. Furthermore, since the difference of the output voltage of the LDR occurred during a period of time of several minutes, one should note that the identification of stool is not immediate.

In summary, the results show that detection of decay in the DC signal level and following that, stabilization in a steady state level, will indicate the presence of stool and/or urine secretion.

In a third experiment (also referred as experiment no. 3), a sensor was positioned on a doll of an infant dressed with an article of clothing (i.e., pants or shirt) put over a diaper. Thus, the sensor was positioned over two layers of garment. Different photodetectors (i.e., LDR, IR 940 nm and a photodiode 565 nm) joined with different colors of LEDs (i.e.: red, green, blue and white) were tested on different colors of garments (i.e., red, green, blue, black and white). The type and thickness of each garment is detailed in the table below:

| Garment Color | Garment Type | Garment thickness |
| --- | --- | --- |
| Red | Cotton | 0.375 mm |
| Green | Cotton | 0.52 mm |
| Blue | Cotton | 0.325 mm |
| Black | Cotton | 0.45 mm |
| White | Cotton | 0.45 mm |

Water was injected into the diaper and the difference in the photodetectors output, while utilizing different colors of LED on different colors of garments was measured.

FIGS. 12A to 12E show graphs of a LDR (P/N:PDV5001 made by Advanced Photonix) output voltage vs. time as a result of a 645 nm red LED (P/N:HT-191URO made by Harvatek) illumination on red, white, black, green and blue garments correspondingly. The received voltage outputs in millivolts from t=0 (time identified as the time of the occurrence) to t=steady state, was 16 during one minute, 20 during one minute, 3.5 during one minute, 5 during one minute and 10 during one minute correspondingly.

FIGS. 13A to 13E show graphs of an LDR output voltage vs. time as a result of a 565 nm green LED (P/N:SML-LX0603GW made by Lumex) illumination on blue, white, black, green and red garments correspondingly. The received voltage outputs in millivolts from t=0 to t=steady state were: 0 during one minute, 5 during one minute, 4 during one minute. 4 during one minute, and 0 during three seconds correspondingly.

FIGS. 14A to 14E show graphs of an LDR output voltage vs. time as a result of a 475 nm blue LED (P/N: QTLP6010EBTR made by Everlight) illumination on red, white, black, green and blue garments correspondingly. The received voltage outputs in millivolts from t=0 to t=steady state were: 1 during one minute, 6 during one minute, 3 during one minute. 3 during one minute, and 1 during three seconds correspondingly.

FIGS. 15A to 15E show graphs of an LDR output voltage vs. time as a result of a white LED (P/N:HT-F199TW5 made by Harvatek) illumination on red, white, black, green and blue garments correspondingly. The received voltage outputs in millivolts from t=0 to t=steady state were: 7 during one minute, 2 during one minute, 1 during one minute, 1 during one minute and 4 during one minute correspondingly.

FIGS. 16A to 16E show graphs of an IR photodetector (P/N: QRE1113GR made by Fairchild) output voltage vs. time as a result of a red LED illumination on red, white, black, green and blue garments correspondingly. The received voltage outputs in millivolts from t=0 to t=steady state were: 25 during one minute, 30 during one minute, 10 during one minute. 20 during one minute and 35 during one minute correspondingly.

Figure 17:
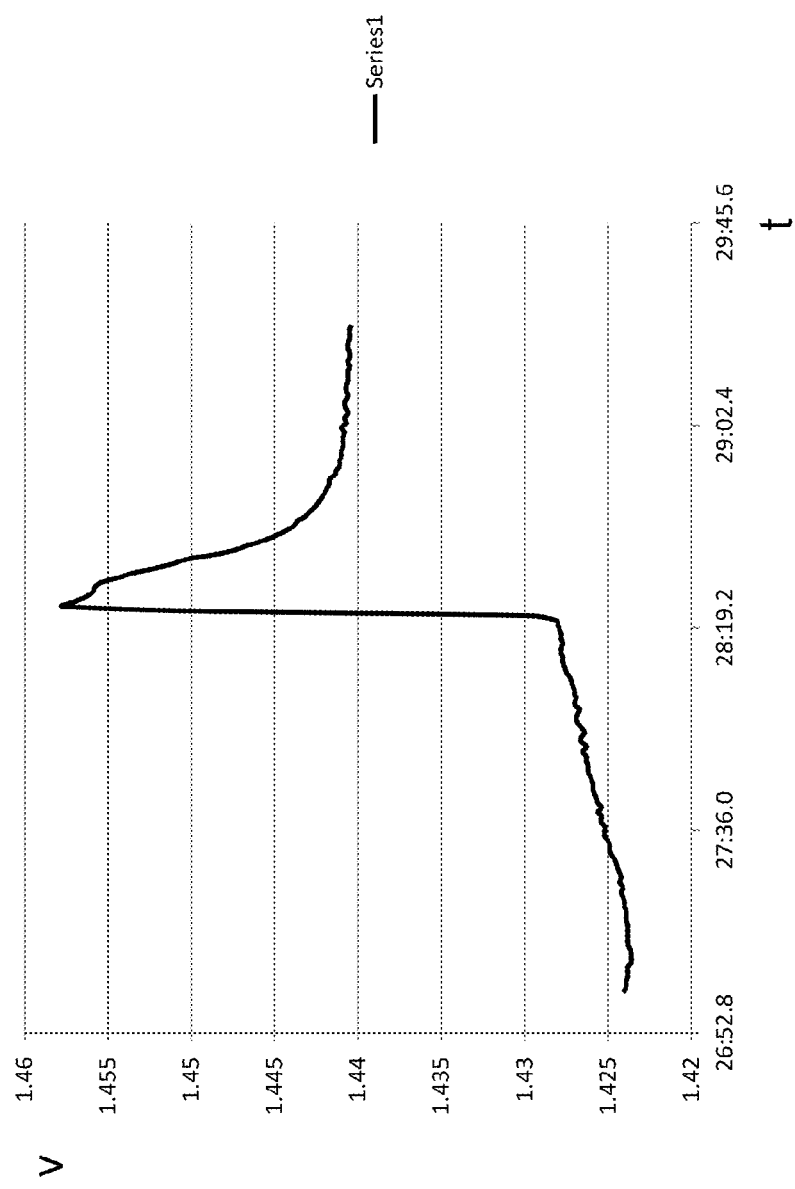
FIG. 17 shows a graph of an IR photodetector output voltage vs. time positioned on a doll dressed with a non-illuminated white garment.
Figure 18A:
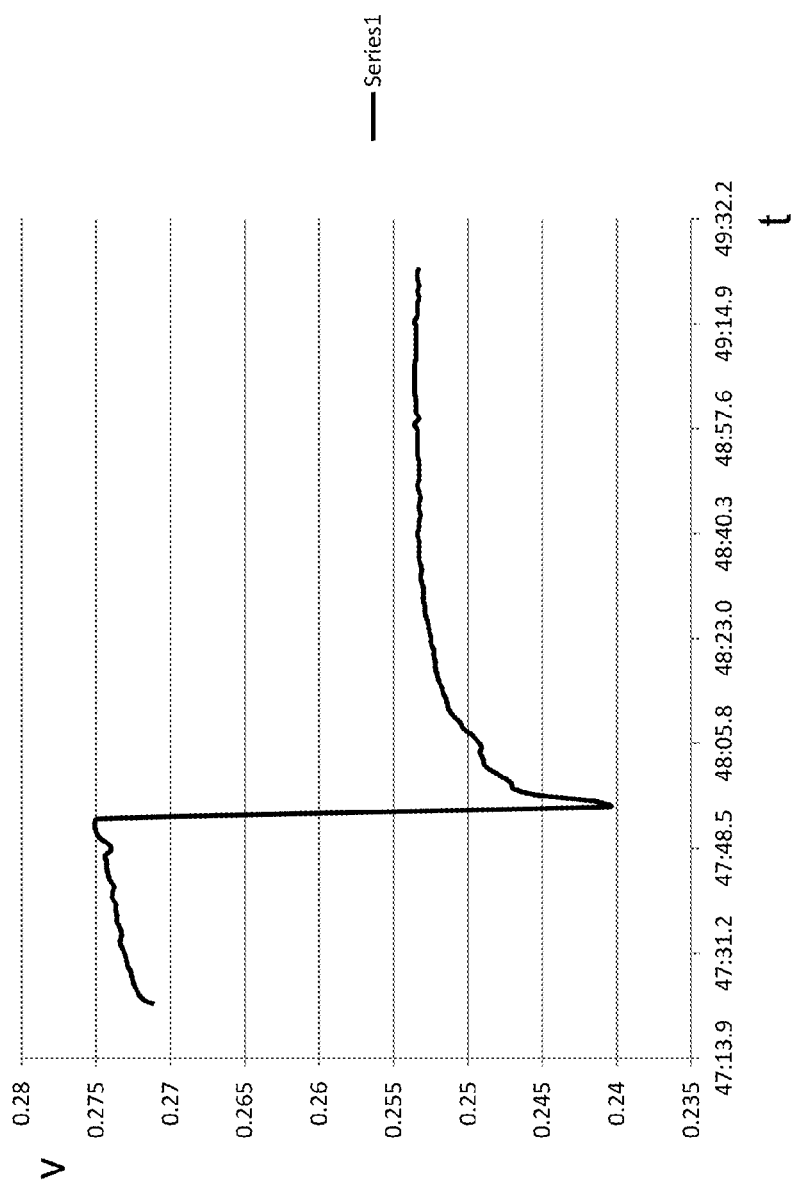
FIG. 18A to 18E show graphs of a photodiode output voltage vs. time positioned on a doll dressed with a non-illuminated white, black, green, red and blue garments correspondingly.
Figure 18B:
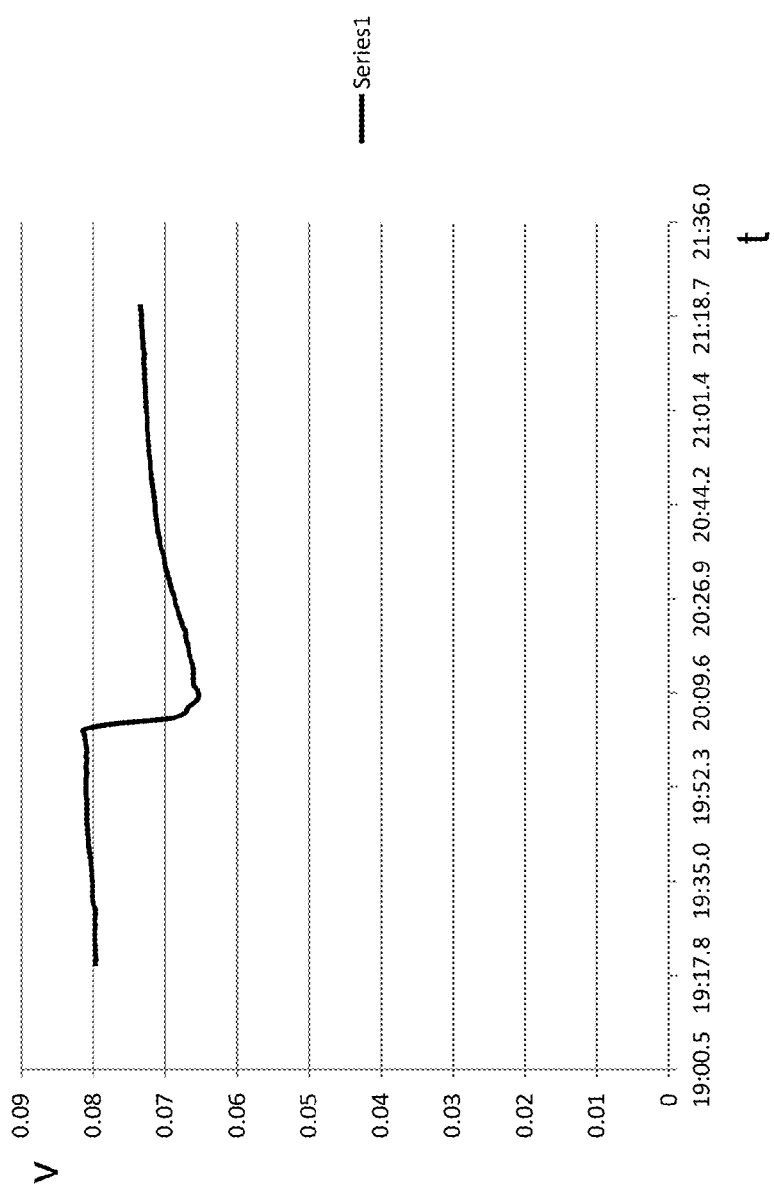
Figure 18C:
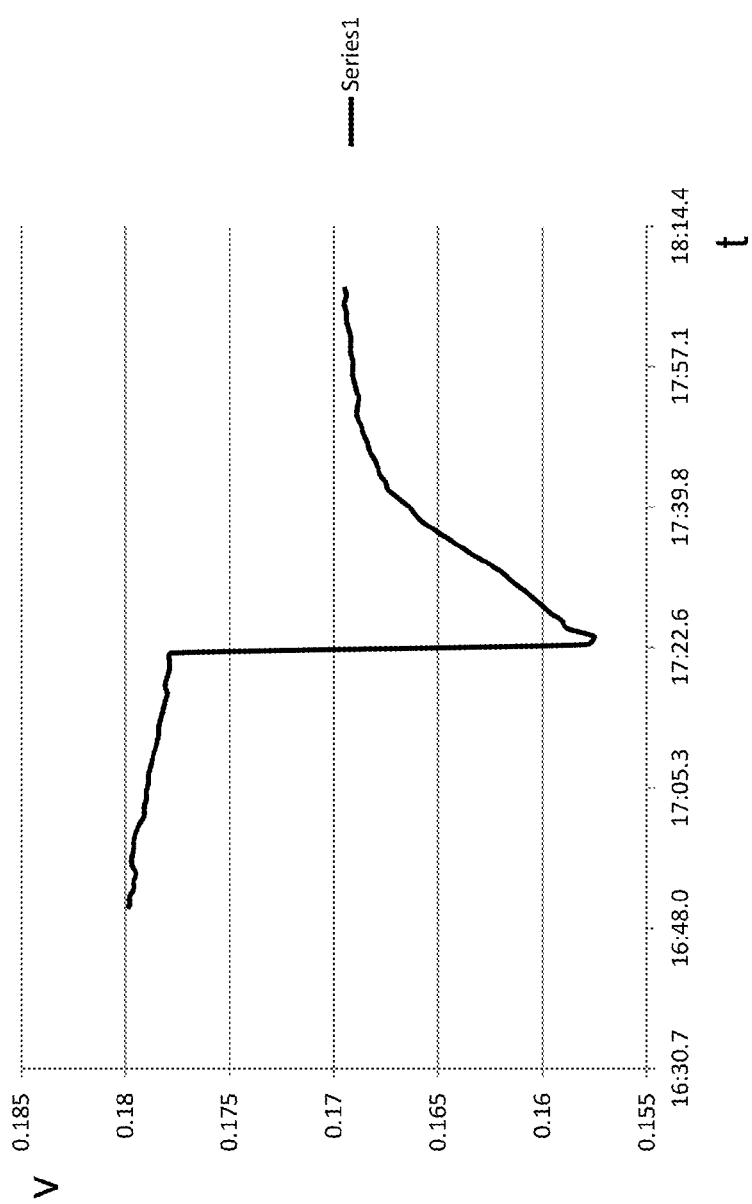
Figure 18D:
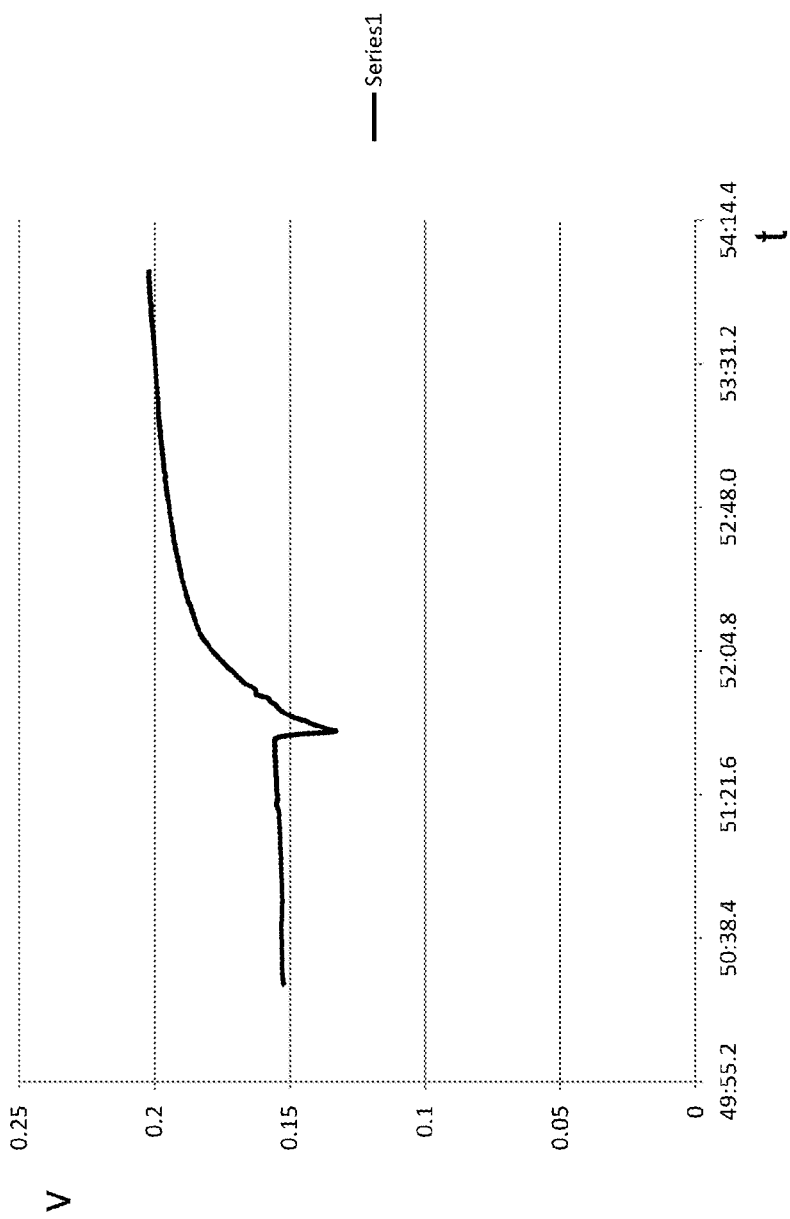
Figure 18E:
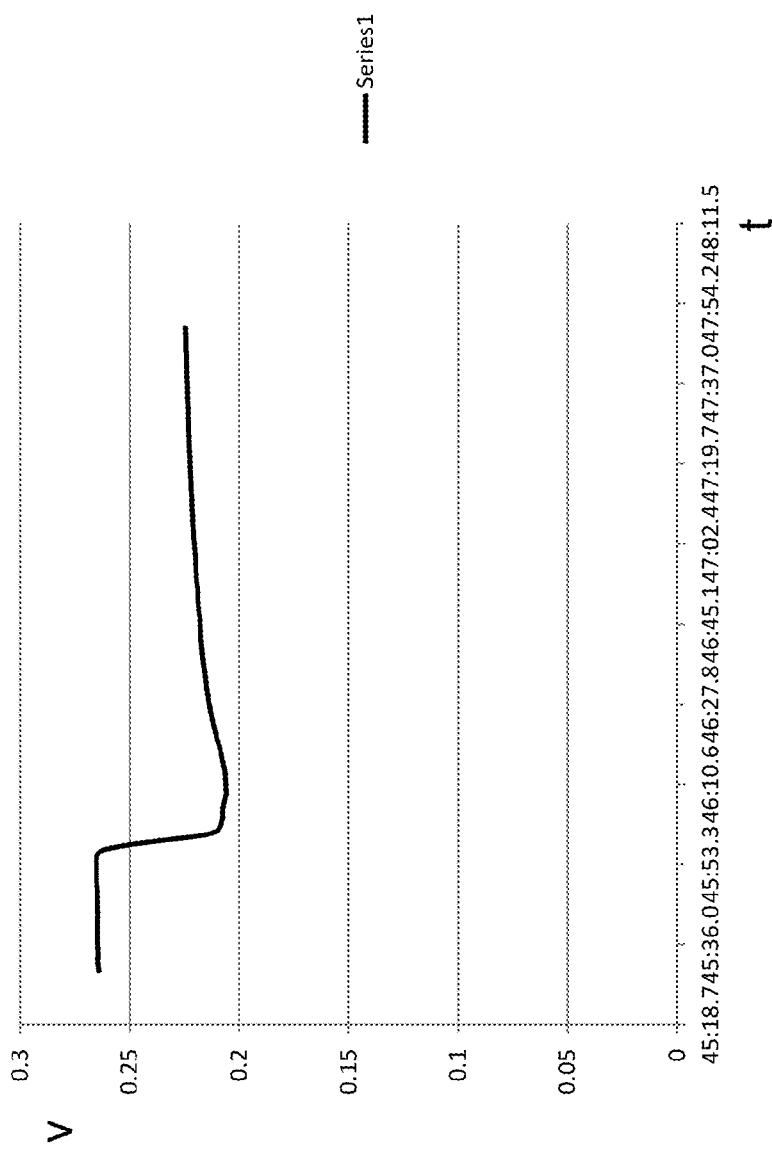

FIG. 17 shows a graph of an IR photodetector output voltage vs. time positioned on a doll dressed with a non-illuminated white garment. The received voltage output in millivolts from t=0 to t=steady state was 13 during one minute.

FIGS. 18A to 18E show graphs of a photodiode output voltage vs. time positioned on a doll dressed with a non-illuminated white, black, green, red and blue garments correspondingly. The received voltage outputs in millivolts from t=0 to t=steady state were: 20 during one minute, 5 during one minute, 10 during one minute. 50 during one minute and 45 during one minute correspondingly.

Figure 19:
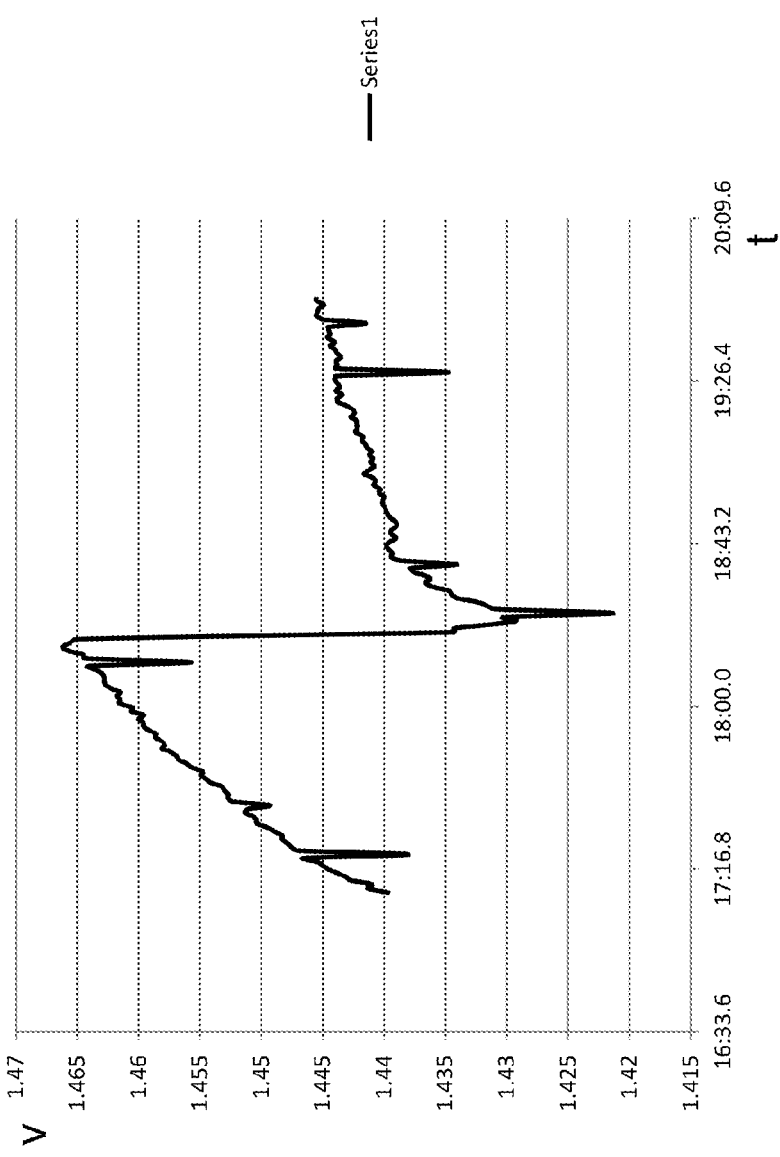
FIG. 19 shows a graph of a photodiode output voltage vs. time as a result of a white LED illumination on a white garment.

FIG. 19 shows a graph of a photodiode (P/N: TEMT6200FX01 made by Everlight) output voltage vs. time as a result of a white LED illumination on white garment. The received voltage output in millivolts from t=0 to t=steady state was 20 during one minute.

Figure 20A:
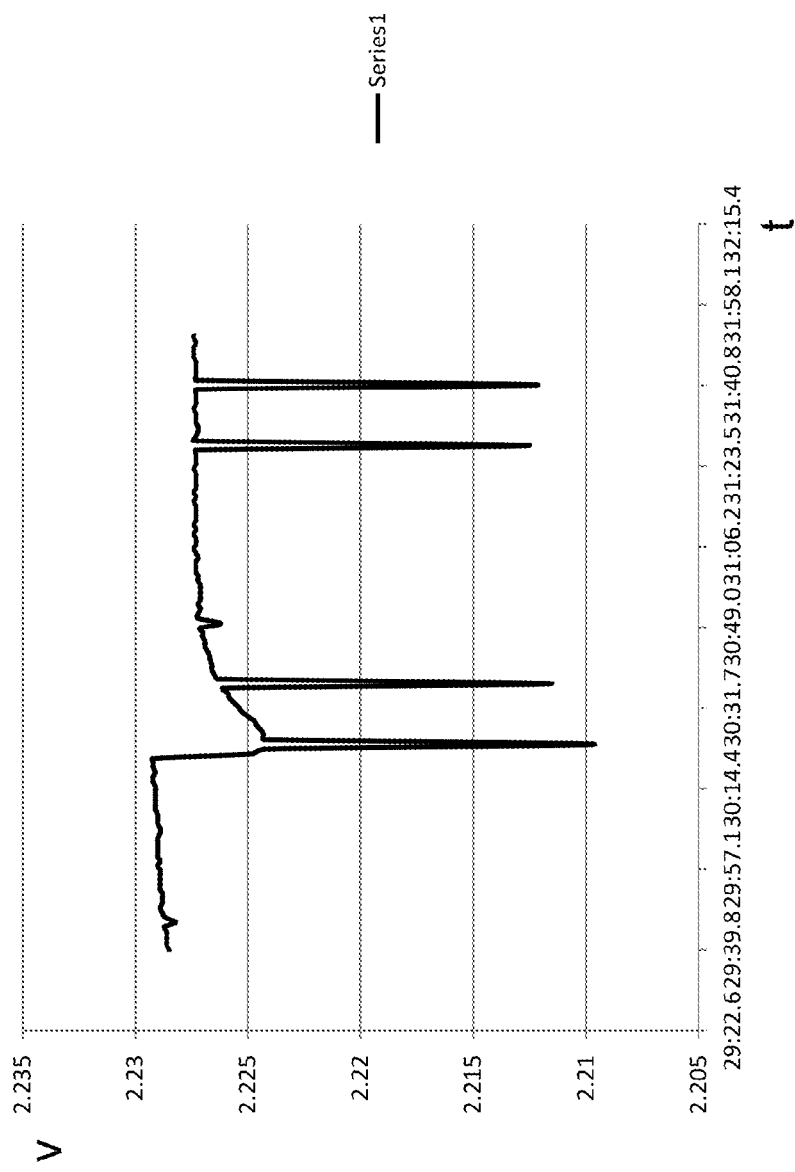
FIGS. 20A and 20B show graphs of an LDR output voltage vs. time as a result of a red LED illumination on white and black garments correspondingly.
Figure 20B:
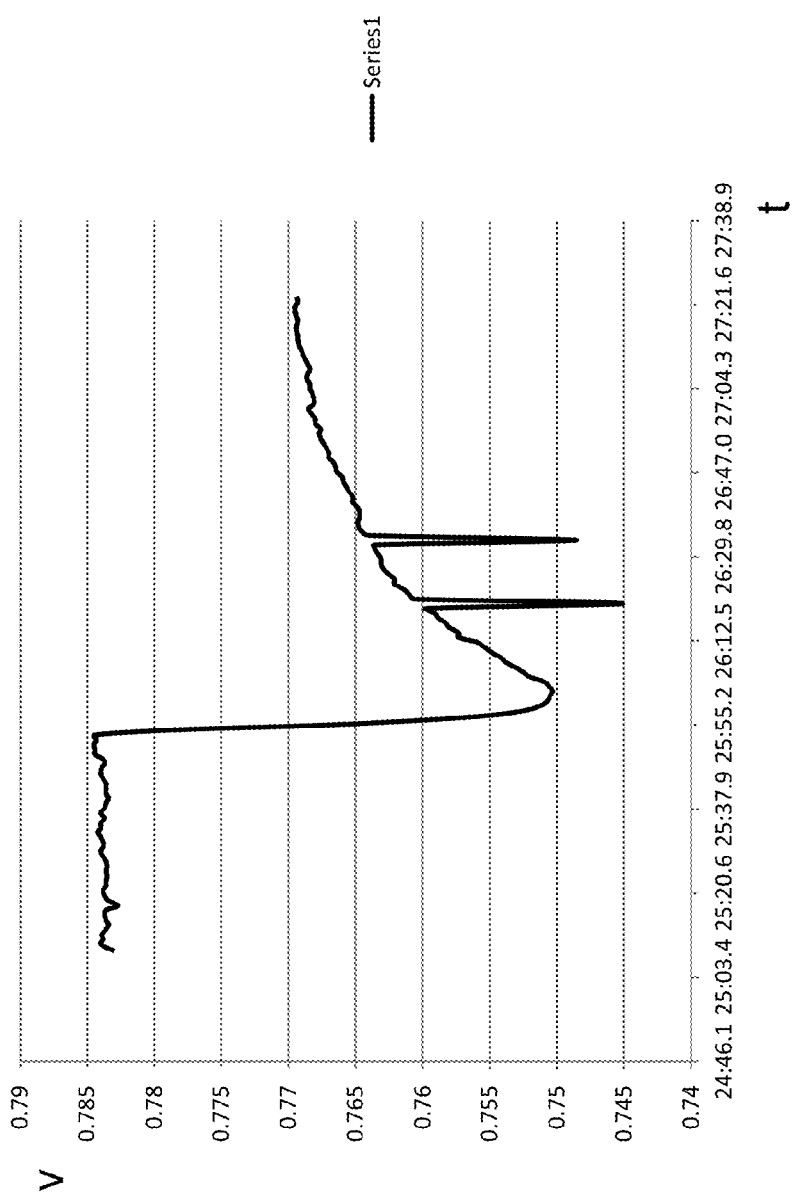

FIGS. 20A and 20B show graphs of a LDR output voltage vs. time as a result of a red LED illumination on white and black garments correspondingly. The received voltage outputs in millivolts from t=0 to t=steady state were 20 during one minute and 15 during one minute.

A table summarizing all of the above results is presented below:

| Photodetector | Illumonation Spectrum | red garment | white garment | black garment | green garment | blue garment | Total Output |
| --- | --- | --- | --- | --- | --- | --- | --- |
| LDR | red | 16 | 20 | 3.5 | 5 | 10 | 54.5 |
| | green | 0 | 5 | 4 | 4 | 0 | 18 |
| | blue | 1 | 6 | 3 | 3 | 1 | 14 |
| | white | 7 | 2 | 1 | 1 | 4 | 15 |
| IR | red | 25 | 30 | 10 | 20 | 35 | 120 |
| | no led | — | 13 | — | — | — | * |

-continued

| Photodetector | Illumonation Spectrum | red garment | white garment | black garment | green garment | blue garment | Total Output |
|---|---|---|---|---|---|---|---|
| Photodiode | white | — | 20 | — | — | — | * |
| | red | — | 20 | 15 | — | — | * |
| | no led | 50 | 20 | 5 | 10 | 45 | * |
| | garment thickness | 0.375 | 0.45 | 0.45 | 0.52 | 0.325 | |

One can see that detection of urine secretion may be performed through two layers of garment: a diaper and an article of clothing such as pants or shirt. Furthermore, one can see that when using an LDR, a red LED provides the highest output with respect to different color garments. The highest output was received when an IR photodetector was used in conjoint with a red LED with respect to different color garments. When a photodiode was used, the highest output was received when there was no illumination. In addition, one can see that the thickness of the garment did not affect the output.

Figure 21:
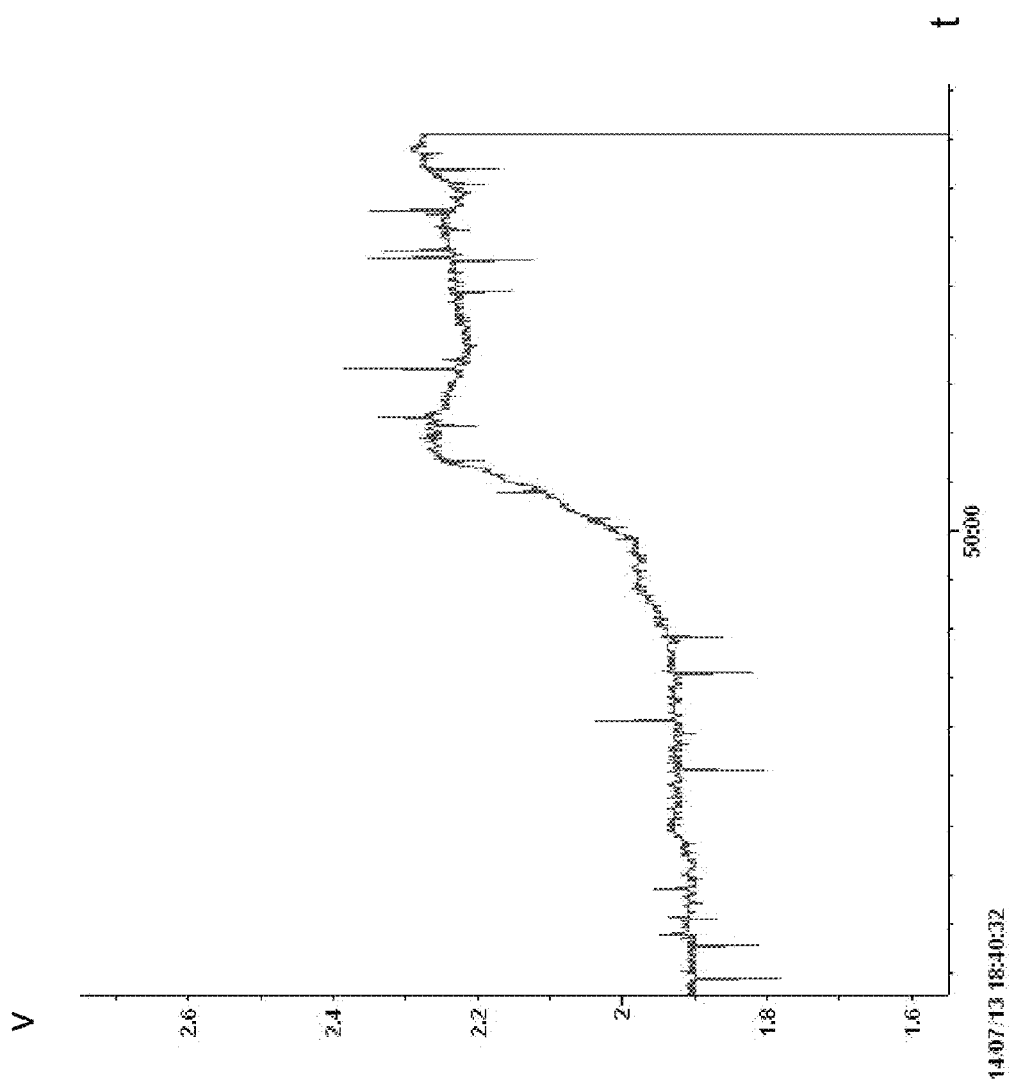
FIG. 21 shows a graph of output voltage vs. time of a sensor configuration including a capacitive detector mounted to a diaper put on an infant during a period of time in which the infant defecated.

In a forth experiment (also referred as experiment no. 4), a capacitive sensor (P/N:HIH-4030 made by Honeywell) was positioned on the bottom part of the diaper. During a period of time, shown in FIG. 21, the infant defecated and stool was found in the diaper. Reference is now made to FIG. 21 which shows the output voltage of the capacitive sensor. One can see that at the relevant time (i.e., time of defecation), started at minute '50, a difference of 350 mV is shown in the output voltage of the capacitive sensor. Furthermore, since the difference of the output voltage occurred during a period of time of less than a minute, one should note that the identification of stool is immediate.

Figure 22:
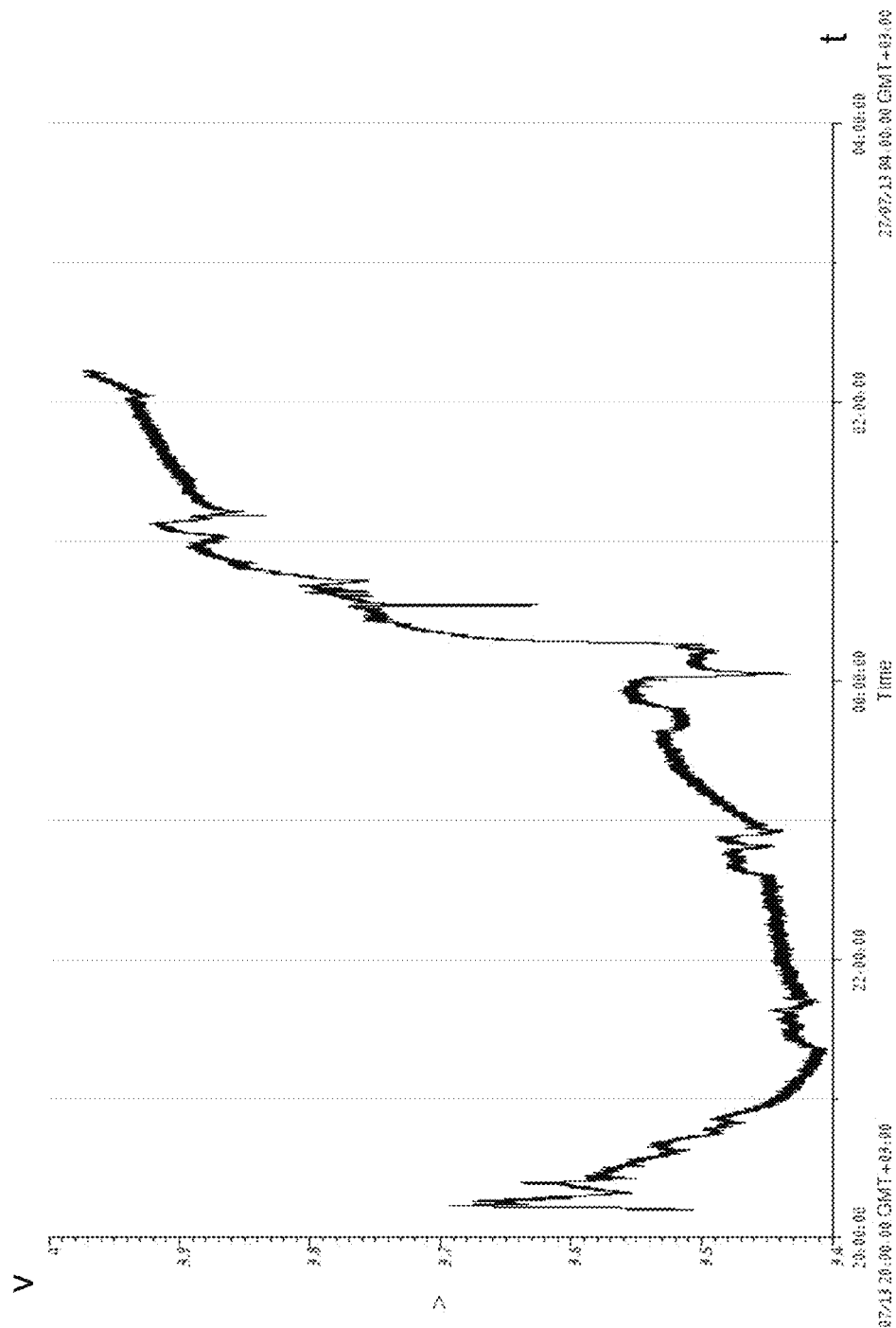
FIG. 22 shows a graph of output voltage vs. time of a sensor configuration including a capacitive detector mounted to a two layers of cloths, put on an infant during a period of time in which the infant defecated.

In a fifth experiment (also referred as experiment no. 5) a capacitive sensor (P/N:HIH-4030 made by Honeywell) was positioned on the bottom part of a diaper. During a period of time, shown in FIG. 22, the infant defecated and stool was found in the diaper. Reference is now made to FIG. 22 which shows the output voltage of the capacitive sensor. One can see that at the relevant time (i.e., time of defecation), started at minute '00, a difference of 400 mV is shown in the output voltage of the capacitive sensor. Furthermore, since the difference is approx 100 mV of the output voltage occurred during a period of time of several minutes, one should note that the identification of stool is very fast.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A sensor,
    wherein the sensor is configured to detect both urine and stool, the sensor comprising:
    a housing configured to attach to a plurality of garment layers, containing
    a) at least one light source configured to illuminate the plurality of garment layers with visible light, whereby the visible light reflects off the plurality of garment layers;
    b) at least one visible wavelength photodetector configured to receive the reflected visible light and output an indication of an amount of the reflected visible light over time,
    wherein the amount of the reflected visible light is altered by the presence of either urine, stool, or both urine and stool; and
    c) an electronic circuit configured to analyze the output of the at least one visible wavelength photodetector and detect a presence of urine or stool in the plurality of garment layers, the detecting being based on a change in the output of the at least one visible wavelength photodetector exceeding a first threshold value, the first threshold value representing a magnitude of the change in the output of the at least one visible wavelength photodetector, the electronic circuit further configured to distinguish between urine and stool by evaluating a slope of the output of the at least one visible wavelength photodetector with respect to time, the electronic circuit identifying urine if the slope exceeds a second threshold value and identifying stool if the slope does not exceed the second threshold value, the second threshold value representing a rate of the change in the output of the at least one visible wavelength photodetector.

2. The sensor according to claim 1, wherein said at least one light source comprises a LED (Light Emitting Diode).

3. The sensor according to claim 1, wherein said at least one visible wavelength photodetector comprises an LDR (Light Dependent Resistor), a CCD, a CMOS, a photovoltaic cell, a photodiode, or a phototransistor.

4. The sensor of claim 1, further comprising a housing with a curved bottom shape.

5. A sensor,
    wherein the sensor is configured to detect both urine and stool, the sensor comprising:
    a housing configured to attach to a plurality of garment layers, containing
    a) at least one capacitive sensor configured to detect changes in humidity of the plurality of garment layers over time,
    wherein the humidity of the plurality of garment layers is altered by the presence of either urine, stool, or both urine and stool; and
    b) an electronic circuit configured to monitor the output of the at least one capacitive sensor and detect a presence of urine or stool in the plurality of garment layers, the detecting being based on a change in the output of the at least one capacitive sensor exceeding a first threshold value, the electronic circuit further configured to distinguish between urine and stool by evaluating a slope of the output of the at least one capacitive sensor with respect to time, the electronic circuit identifying urine if the slope exceeds a second threshold value and identifying stool if the slope does not exceed the second threshold value.

6. The sensor of claim 5, further comprising a housing with a curved bottom shape.

7. The sensor of claim 1, wherein the threshold value is predetermined.

8. The sensor of claim 7, wherein the threshold value is predetermined based on a type of the plurality of garment layers.

9. The sensor of claim 8, wherein the threshold value is predetermined based on a material characteristic of the type of the plurality of garment layers.

10. The sensor of claim 1, wherein the threshold value is determined by a calibration performed when the sensor is attached to the plurality of garment layers.

* * * * *